US009428753B2

(12) United States Patent
Cummins et al.

(10) Patent No.: US 9,428,753 B2
(45) Date of Patent: Aug. 30, 2016

(54) USE OF LXR ANTAGONISTS FOR TREATMENT OF SIDE EFFECTS OF ELEVATED GLUCOCORTICOID LEVELS

(71) Applicants: The Governing Council of the University of Toronto, Toronto (CA); Fernado A. Fernandez, Etobicoke (CA); Arturo Orellana, Toronto (CA)

(72) Inventors: Carolyn Cummins, Toronto (CA); Arturo Orellana, Toronto (CA); Rucha Patel, Toronto (CA); Fernando A. Fernandez, Toronto (CA)

(73) Assignees: THE GOVERNING COUNCIL OF THE UNIVERSITY OF TORONTO, Toronto (CA); Fernando A. Fernandez, Etobicoke (CA); Arturo Orellana, Toronto (CA)

(*) Notice: Subject to any disclaimer, the term of this patent is extended or adjusted under 35 U.S.C. 154(b) by 31 days.

(21) Appl. No.: 14/178,384

(22) Filed: Feb. 12, 2014

(65) Prior Publication Data
US 2014/0271673 A1 Sep. 18, 2014

Related U.S. Application Data

(60) Provisional application No. 61/792,502, filed on Mar. 15, 2013.

(30) Foreign Application Priority Data

Jun. 21, 2013 (CA) ..................................... 2819448

(51) Int. Cl.
| | | |
|---|---|---|
| A61K 31/341 | (2006.01) | |
| A61K 31/18 | (2006.01) | |
| A61K 31/573 | (2006.01) | |
| C07J 41/00 | (2006.01) | |
| C12N 15/113 | (2010.01) | |

(52) U.S. Cl.
CPC ........... *C12N 15/1138* (2013.01); *A61K 31/18* (2013.01); *A61K 31/341* (2013.01); *A61K 31/573* (2013.01); *C07J 41/0061* (2013.01)

(58) Field of Classification Search
None
See application file for complete search history.

(56) References Cited

U.S. PATENT DOCUMENTS

2006/0178398 A1  8/2006  Adams et al.

FOREIGN PATENT DOCUMENTS

| JP | 2006315997 A | 11/2006 |
|---|---|---|
| JP | 2011102240 A | 5/2011 |
| WO | 2006104826 A2 | 10/2006 |
| WO | 2007081335 A1 | 7/2007 |
| WO | 2008041003 A2 | 4/2008 |
| WO | 2008078099 A1 | 7/2008 |
| WO | 2009115212 A1 | 9/2009 |

OTHER PUBLICATIONS

Janowski, Bethany A., et al., "Structural requirements of ligands for the oxysterol liver X receptors LXRa and LXRB", Proc. Natl. Acad. Sci. USA, vol. 96, Jan. 1999, pp. 206-271.
Chachra, D., et al., "The Effect of Different Hormone Replacement Therapy Regimens on the Mechanical Properties of Rat Vertebrae", Calcif. Tissue Int., (1995), 56, pp. 130-134.
Clarke, Brian A., et al., "The E3 Ligase MuRF1 Degrades Myosin Heavy Chain Protein in Dexamethasone-Treated Skeletal Muscle", Cell Metabolism 6, Nov. 2007, pp. 376-385.
Omelon, Sidney, et al., "Control of Vertebrate Skeletal Mineralization by Polyphosphates", PLoS One, May 2009, vol. 4, Issue 5, pp. 1-16.
Watson, Monica L., et al., "A cell-autonomous role for the glucocorticoid receptor in skeletal muscle atrophy induced by systemic glucocorticoid exposure", Am J Physiol Endocrinol Metab, 302, Feb. 21, 2012, pp. 1210-1220.
Zuercher, William J., et al., "Discovery of Teritiary Sulfonamides as Potent Liver X Receptor Antagonist", J Med. Chem. 2010, 53, pp. 3412-3416.
Bracci, Paige M., et al., "Analysis of Compositional Bone Density Data Using Log Ratio Transformations", Biometrics, 54, Mar. 1998, pp. 337-349.
Imai, Enyu, et al, "Glucocorticoid Receptor-cAMP Response Element-Binding Protein Interaction and the Response of the Phosphoenolpyruvate Carboxykinase Gene to Glucocorticoids", The Journal of Biological Chemistry, vol. 268, No. 8, Mar. 15, 1993, pp. 5353-5356.
Arner, Peter, et al, "Some Characteristics of Steroid Diabetes: A Study in Renal-Transplant Recipients Receiving High-Dose Corticosteroid Therapy", Diabetes Care, vol. 6, No. 1, Jan.-Feb. 1983, pp. 23-25.
Bdolah, Yuval, et al, "Atrophy-related ubiquitin ligases atrogin-1 and MuRF-1 are associated with uterine smooth muscle involution in the postpartum period", Am J. Physiol Regul Integr Comp Physiol, 292, Sep. 28, 2006, pp. R971-R976.
Bhansali, A, et al, "Ectopic Cushing's syndrome: Experience from a tertiary care centre", Indian J Med Res 129, Jan. 2009, pp. 33-41.
Boissan, Mathieu, et al, "Tumorigenesis and Neoplastic Progression: Overexpression of Insulin Receptor Substrate-2 in Human and Murine Hepatocellular Carcinoma", American Journal of Pathology, vol. 167, No. 3, Sep. 2005, pp. 869-877.
Cassuto, Hanoch, et al, "Genes Structure and Regulation: Glucocorticoids Regulate Transcription of the Gene for Phosphoenolpryuvate Carboxykinase in the Liver via an Extended Glucocorticoide Regulatory Unit", The Journal of Biological Chemistry, 280, Aug. 12, 2005, pp. 33873-33884.

(Continued)

*Primary Examiner* — Ruixiang Li
(74) *Attorney, Agent, or Firm* — Bereskin & Parr LLP/S.E.N.C.R.L., s.r.l.; Patricia Folkins

(57) ABSTRACT

The present application is directed to uses of an agent that antagonizes the LXRβ receptor for the treatment of side effects associated with elevated glucocorticoid levels as well as uses of a glucocorticoid in combination with the agent that antagonizes the LXRβ receptor for treatment of a disease wherein glucocorticoid treatment is indicated.

24 Claims, 10 Drawing Sheets

(56) References Cited

OTHER PUBLICATIONS

Chakravarty, Kaushik, et al, "Factors That Control the Tissue-Specific Transcription of the Gene for Phospoenolpyruvate Carboxykinsase-C", Critical Reviews in Biochemistry and Molecular Biology, 40, 2005, pp. 129-154.

Chan, Timothy M., et al, "A Rapid Method for the Determination of Glycogen Content and Radioactivity in Small Quantities of Tissue or Isolated Hepatocytes", Analytical Biochemistry 71, (1976), pp. 96-105.

Commerford, Renee S., et al, "Dissection of the Insulin-Sensitizing Effect of Liver X Receptor Ligands", Molecular Endocrinology 21(12), Dec. 2007, pp. 3002-3012.

Dempster, David W., et al, "Standardized Nomenclature, Symbols, and Units for Bone Histomorphometry: A 2012 Update of the Report of the ASBMR Histomorphometry Nomenclature Committee", Journal of Bone and Mineral Research, vol. 28, No. 1, Jan. 2013, pp. 1-16.

Hall, Robert, K. et al, "The orphan receptors COUP-TF and HNF-4 serve as accessory factors required for induction of phosphoenolpyruvate carboxykinase gene transcription by glucocorticoids", Proc. Natl. Acad. Sci. USA, vol. 92, Jan. 1995, pp. 412-416.

Hall, Robert, K, et al, "Insulin Represses Phosphoenolpyruvate Carboxykinase Gene Transcription by Causing the Rapid Disruption of an Active Transcription Complex: A Potential Epigenetic Effect", Molecular Endocrinology 21(2), Feb. 2007, pp. 550-563.

Herzog, Birger, et al, "The Nuclear Receptor Cofactor, Receptor-Interacting Protein 140, Is Required for the Regulation of Hepatic Lipid and Glucose Metabolism by Liver X Receptor", Molecular Endocrinology 21(11), Nov. 2007, pp. 2687-2697.

Howlett, T.A., et al, "Cushing's Syndrome", Clinics in Endocrinology and Metabolism—vol. 14, No. 4, Nov. 1985, pp. 911-945.

Kalaany, Nada, Y., et al, "LXRs regulate the balance between fat storage and oxidation", Cell Metabolism, vol. 1, Apr. 2005, pp. 231-244.

Kaltsas, Gregory, et al, "Osteoporosis in Cushing's Syndrome", Part II. Clinical Aspects and Epidemiology, Giustina, Angeli, A. et al, (eds): Glucocorticoid—Induced Osteoporosis, Front Horn,Res., 2002, vol. 30, pp. 60-72.

Kasra, M., et al, "Effects of Different Estrogen and Progestin Regimens on the Mechanical Properties of Rat Femur", Journal of Orthopedic Research, vol. 15, No. 1, 1997, pp. 118-123.

Kauh, Eunkyung, et al, "Prednisone affects inflammation, glucose tolerance, and bone turnover within hours of treatment in healthy individuals", European Journal of Endocrinology 166, 2012, pp. 459-467.

Kim, Ja-Young, et al, "Obesity- associated improvements in metabolic profile through expansion of adipose tissue", The Journal of Clinical Investigation, vol. 117, No. 9, Sep. 2007, pp. 2621-2637.

Kyle, Kimberly A., et al, "Differential Effects of PPAR-y Activation versus Chemical or Genetic Reduction of DPP-4 Activity on Bone Quality in Mice", Endocrinology, 152(2), Feb. 2011, pp. 457-467.

Liu, Yanjun, et al, "Liver X Receptor Agonist T0901317 Inhibition of Glucocorticoid Receptor Expression in Hepatocytes May Contribute to the Amelioration of Diabetic Syndrome in db/db Mice", Endocrinology 147(11), Nov. 2006, pp. 5061-5068.

Mancini, Tatiana, et al, "Cushing's Syndrome and Bone", Pituitary 7, 2004, pp. 243-246.

Miner, Jeffrey, N, et al, "The basic region of AP-1 specifies glucocorticoid receptor activity at a composite response element", Genes & Developement 6, 1992, pp. 2491-2501.

Mousny, M. et al, "The genetic influence on bone susceptibilty to fluoride", Bone 39, 2006, pp. 1283-1289.

Mousny, M, et al, "Fluoride Effects on Bone Formation and Mineralization are Influenced by Genetics", Bone, 43(6), Dec. 2008, pp. 1067-1074.

Nieman, Lynnette, K. "Diagnostic Tests for Cushing's Syndrome", Ann, N.Y. Acad. Sci. 970, 2002, pp. 112-118.

Ohmori, Nariko, et al, "Osteoporosis is More Prevalent in Adrenal than in Pituitary Cushing's Syndrome", Endocrine Journal, 50 (1), 2003, pp. 1-7.

Patel, Rucha, et al, "LXRB is required for glucocorticoid-induced hyperglycemia and hepatosteatosis in mice", The Journal of Clinical Investigation, vol. 121, No. 1, Jan. 2011, pp. 431-441.

Puigserver, Pere, et al, "Insulin-regulated hepatic gluconeogenis through FOX01-PGC-1a interaction", Nature, vol. 423, May 2003, pp. 550-555.

Reid, Ian R., et al, "Determinants of Vertebral Mineral Density in Patients Receiving Long-term Glucocorticoid Therapy", Arch Intern Med, vol. 150, Dec. 1990, pp. 2545-2548.

Roesler, William J, "What is a cAMP response unit?", Molecular and Cellular Endocrinology, 162, 2000, pp. 1-7.

Sandri, Marco, et al, "Foxo Transcription Factors Induce the Atrophy-Related Ubiquitin Ligase Atrogin-1 and Cause Skeletal Muscle Atrophy", Cell, 117(3), Apr. 2004, pp. 399-412.

Scott, Donald K., et al, "Nucleic Acids, Protein Synthesis, and Molecular Genetics: The Orphan Receptor COUP-TF Binds to a Third Glucorticoid Accessory Factor Element within the Phosphoenolpyruvate Carboxykinase Gene Prompter", The Journal of Biological Chemistry, 271, 1996, pp. 31909-31914.

Scott, Donald K., et al, "Cell Biology and Metabolism: The Repression of Hormone-activated PEPCK Gene Expression by Glucose is Insulin-independent but Requires Glucose Metabolism", The Journal of Biological Chemisrty, 273, 1998, pp. 24145-24151.

Sekine, Keisuke, et al, "Foxo1 links insulin signaling to C/EBPa and regulates gluconeogenesis during liver development", The EMBO Journal, 26, 2007, pp. 3607-3615.

Sugiyama, Takashi, et al, "Structural Requirements of the Glucorticoid and Retinoic Acid Response Units in the Phosphoenolpyruvate Carboxykinase Gene Promoter", Molecular Endocrinology, vol. 12, No. 10, 1998, pp. 1487-1498.

Wagner, Brandee, L., et al, "Promoter-Specific Roles for Liver X Receptor/Corepressor Complexes in the Regulation of ABCA1 and SREBP1 Gene Expression", Molecular and Cellular Biology, vol. 23, No. 16, Aug. 2003, pp. 5780-5789.

Waltner-Law, Mary, et al, "Genes Structure and Regulation- Elements of the Glucorticoid and Retinoic Acid Response Units Are Involved in cAMP-mediated Expression of the PEPCK Gene", The Journal of Biological Chemistry, 278, 2003, 10427-10435.

Wang, Jen Chywan, et al, "Genes: Structure and Regulation: The Molecular Physiology of Hepatic Nuclear Factor 3 in the Regulation of Gluconeogenesis", The Journal of Biological Chemistry, 275, 2000, pp. 14717-14721.

Patel, Rucha, et al., "LRXB is Required for Glucocorticoid-induced Hyperglycemia and Hepatosteatosis", Keystone Symposium on Nuclear Receptors, Keystone, Co., Mar. 2010.

Cummins, Carolyn L., "LXRβ in Glucocorticoid-Induced Hyperglycemia and Hepatic Steatosis", Faculty of Pharmacy, University of Toronto, Nov. 2010.

Cummins, Carolyn L., "Importance of LXRβ in Glucocorticoid-Mediated Hepatic Steatosis and Hyperglycemia", University of Western Ontario, London, ON, Feb. 7, 2011.

Cummins, Carolyn L, "LXRβ is Required for Glucocorticoid-Induced Hyperglycemia and Hepatosteatosis", 3rd Annual Endocrinology and Diabetes Research Group Scientific Day, Toronto, ON, Jun. 14, 2010.

Cummins, Carolyn L., et al., "Liver X receptors regulate adrenal cholesterol balance", J Clin Invest, 2006, 116(7), pp. 1902-1912.

Laffitte, Bryan A., et al., "Activation of liver X receptor improves glucose tolerance through coordinate regulation of glucose metabolism in liver and adipose tissue", Proc Natl Acad Sci USA, 2003, 100(9), pp. 5419-5424.

Grefhorst, Aldo, et al., "Differential effects of pharmacological liver X receptor activation on hepatic and peripheral insulin sensitivity in lean and ob/ob mice", Am J Physiol Endocrinol Metab, 2005, 289(5), pp. E829-E838.

Bookout, Angie L., et al., "Anatomical profiling of nuclear receptor expression reveals a hierarchical transcriptional network", Cell, 2006, 126(4), pp. 789-799.

Nadar, Nancy, et al., "Liver X receptors regulate the transcriptional activity of the glucocorticoid receptor: implications for the carbohydrate metabolism", PLoS One, 2012, 7(3), pp. e26751.

Flaveny, C.A., et al., Broad Anti-tumor Activity of a Small Molecule that Selectively Targets the Warburg Effect and Lipogenesis. Cancer Cell, 2015, 28(1), pp. 42-56 and Supplemental Information pp. 1-32.

A

B

C

D

Legend:
V = Vehicle
G = GSK2033 compound (LXR antagonist)
D = Dexamethasone (GR agonist)
T09 = T0901317 (LXR agonist)

Legend:
V = Vehicle
G = GSK2033 compound (LXR antagonist)
D = Dexamethasone (GR agonist)

Legend:
Veh = Vehicle
Dex = Dexamethasone (GR agonist)
G = GSK2033 compound (LXR antagonist)

Legend:
V = Vehicle
Dex = Dexamethasone (GR agonist)
CL = DMHCL (LXR antagonist)
AM = AMGEN54 (LXR antagonist)
G = GSK2033 compound (LXR antagonist)

Legend:
Veh = Vehicle
G = GSK2033 compound (LXR antagonist)
T09 = T0901317 (LXR agonist)

USE OF LXR ANTAGONISTS FOR TREATMENT OF SIDE EFFECTS OF ELEVATED GLUCOCORTICOID LEVELS

CROSS-REFERENCE TO RELATED APPLICATIONS

The present application claims the benefit of priority from co-pending U.S. provisional application no. 61/792,502 filed on Mar. 15, 2013 and Canadian patent application no. 2,819,448 filed on Jun. 21, 2013, the contents of both of which are incorporated herein by reference in their entirety.

FIELD OF THE APPLICATION

The present application relates to the use of LXR antagonists for the treatment of side effects associated with elevated glucocorticoid levels as well as the use of a glucocorticoid in combination with an LXR antagonist for the treatment of a disease wherein glucocorticoid treatment is indicated.

BACKGROUND OF THE APPLICATION

Glucocorticoid (GC) drugs have profound anti-inflammatory and immunosuppressive properties that are useful for treating a wide variety of chronic conditions including, for example, rheumatoid arthritis, inflammatory bowel disease, lupus erythematosus and asthma. Synthetic GCs are among the most widely prescribed drugs in the world. The therapeutic usage of glucocorticoids has risen continuously in recent years. Each year 10 million new prescriptions are written for oral corticosteroids in the United States. Overall, the total market size is considered to reach about 10 billion US dollars per year.

Unfortunately, the development of major side effects remains a key limitation for the long-term therapeutic use of GCs. Common side effects of GCs that require, for example, dosage adjustment or removal from therapy include, insulin resistance, hyperglycemia, diabetes, for example, steroid diabetes, fatty liver (hepatosteatosis), hypertension, bone loss, for example, osteoporosis and muscle wasting. For example, a study has shown that patients receiving high-dose glucocorticoid therapy lost a mean of 27% of their lumbar spine bone density during the first year of treatment.[1] Another study showed that up to 50% of patients receiving GC treatment required insulin as a result of GC-induced diabetes.[2]

Table 1 outlines the current treatments used to reduce GC-induced side effects. These combination therapies are known to have inherent side effects and/or deficiencies in therapeutic outcome.

Hepatic glucose production is essential for survival during times of stress, fasting and starvation. In response to stress, GCs are released from the adrenal cortex, increasing the expression of gluconeogenic genes through activation of the glucocorticoid receptor (GR) in the liver. During fasting, glucagon is secreted from the α-cells of the pancreatic islets. Glucagon signals for the utilization of liver glycogen stores to maintain normoglycemia while also protecting against hypoglycemia through upregulation of genes in the gluconeogenic pathway.

Insulin is the dominant suppressor of gluconeogenesis in response to feeding. Complex signaling orchestrated by fasting, stress and feeding hormones tightly regulate expression of enzymes involved in the gluconeogenic pathway. Several genes regulated by GR in the liver include phosphoenolpyruvate carboxykinase (Pepck) and glucose-6-phosphatase (G6Pc). Pepck and its regulation have been extensively studied due to its importance in hepatic glucose output during fasting and in diabetes.[3] Its expression is mainly regulated at the transcriptional level by complex hormonal and dietary stimuli. Under normal conditions, after a meal, an increase in circulating glucose stimulates insulin secretion from the pancreatic β-cells. In the liver, increased circulating insulin inhibits Pepck transcription through Akt-mediated phosphorylation of FOXO1, resulting in inactivation of this transcription factor and ultimately a suppression of hepatic glucose production.[4] Conversely, Pepck expression is induced in response to fasting through the actions of increased circulating glucagon and GCs.[5] In contrast to the effects of GCs in the liver, studies in diabetic animal models have shown that activation of the liver X receptor (LXR) (with a synthetic agonist) improves glucose tolerance and reduces hepatic glucose output by downregulating the expression of Pepck, G6Pc, 11β-hydroxysteroid dehydrogenase type 1 and GR.[6,7]

Multiple interactions of regulatory factors and co-activators have been characterized within the first 1.5 kb region upstream of the transcription start site (TSS) on the rat Pepck promoter.[5] Induction of Pepck gene expression by GCs is mediated through the complex glucocorticoid response unit (GRU). The GRU is composed of two low affinity, non-consensus GR binding sites (GRE1 and GRE2), a cAMP response element (CRE) binding site, three adjacent glucocorticoid receptor accessory factor binding sites (gAF1, gAF2 and gAF3) and two distal accessory binding sites.[4,8,9,10,11,12]

Several studies have shown that the binding of accessory factors FOXO1, HNF4α, COUP-TF, PPARγ2, PPARα and RXRα/RAR to the glucocorticoid receptor accessory factor binding sites facilitates the binding of GR to the Pepck promoter non-consensus GRE and is necessary for full GC-induced Pepck expression.[11,13] Several coactivators including PGC1α, GRIP-1, SRC-1 and CBP/p300 are also involved in Pepck transactivation, but not all of the coactivators are obligatory for GC-induced Pepck expression.[5,14]

Moreover, the GRU of the Pepck promoter also encompasses a cAMP response unit and a retinoic acid response unit. Furthermore, the gAF2 region of GRU is also a part of the insulin response unit of the gene.[9,15,16] This indicates that the GRU is a more global regulatory element in which all of the sites act in a synergistic manner to control the transcription of the Pepck gene in response to GCs, glucagon, insulin and retinoic acids.

In contrast to the induction of Pepck with GR activation, activation of LXRα by a synthetic ligand (GW3965) represses Pepck expression in mouse liver.[6] Herzog et al. (2007) also showed in a human hepatoma cell line (Huh7) that activation of LXR by a synthetic potent ligand T0901317, recruits LXR and a co-repressor (RIP140) to the endogenous Pepck promoter (gAF3 region) to repress transcription.[17] Together, these studies demonstrate that activation of GR and LXRα reciprocally regulate liver gluconeogenesis.

Mice which lack the expression of LXRβ or both LXRα and LXRβ were found to be resistant to developing dexamethasone (Dex)-induced hyperglycemia, hyperinsulinemia and hepatic steatosis but were still sensitive to the immunosuppressive effects of Dex.[18]

Cushing's syndrome is most frequently caused by a pituitary adenoma that hypersecretes the trophic factor ACTH. In response to ACTH, the adrenal gland becomes enlarged and is stimulated to produce excess cortisol (a glucocorticoid (GC) hormone). Because the pituitary tumour is insensitive to feedback inhibition by cortisol, the stimulating effect of ACTH continues uninterrupted. As such, Cushing's syndrome patients have high circulating endogenous GC levels and many cases present with symptoms of abnormal fat distribution, insulin resistance, hyperglycemia, hypertension (70-90%)[19, 20]; proximal myopathy (30-80%)[19, 21]; and osteoporosis (40%-70%)[19, 22, 23, 24].

SUMMARY OF THE APPLICATION

In the present application, several compounds that act as antagonists of the LXRβ receptor have been shown to reduce the side effects of elevated glucocorticoid (GC) levels, for example, hyperglycemia and hepatosteatosis. When elevated GC levels were due to exogenous administration of a GC, this reduction in side effects was achieved without affecting some of the positive effects of the GCs, such as their immunosuppressive properties. Specifically, in vitro and in vivo studies of the present application have found that pharmacological antagonism of LXRβ suppresses the gluconeogenic side effects associated with glucocorticoids without affecting their immunosuppressive properties.

Accordingly, the present application includes a method of treating a side effect of elevated glucocorticoid levels comprising administering a therapeutically effective amount of an agent that antagonizes the LXRβ receptor to a subject in need thereof.

The present application further includes a use of an agent that antagonizes the LXRβ receptor for treating a side effect of elevated glucocorticoid levels as well as a use of an agent that antagonizes the LXRβ receptor for preparation of a medicament for treating a side effect of elevated glucocorticoid levels. The application also includes an agent that antagonizes the LXRβ receptor for use in treating a side effect of elevated glucocorticoid levels.

In one embodiment, the elevated glucocorticoid levels are the result of elevated endogenous glucocorticoid levels, such as elevated glucocorticoid levels that result from the presence of a condition, disease or disorder, for example Cushing's syndrome, type 2 diabetes and chronic stress.

In another embodiment, the elevated glucocorticoid levels are the result of elevated exogenous glucocorticoid levels, such as elevated glucocorticoid levels that result from administration of a glucocorticoid as a therapeutic agent. Accordingly, the present application also includes a method of treating a disease wherein glucocorticoid treatment is indicated comprising administering a therapeutically effective amount of a glucocorticoid in combination with a therapeutically effective amount of an agent that antagonizes the LXRβ receptor to a subject in need thereof.

The present application further includes a use of a glucocorticoid in combination with an agent that antagonizes the LXRβ receptor for treating a disease wherein glucocorticoid treatment is indicated, as well as a use of a glucocorticoid in combination with an agent that antagonizes the LXRβ receptor for preparation of a medicament for treating a disease wherein glucocorticoid treatment is indicated. The application also includes a glucocorticoid in combination with an agent that antagonizes the LXRβ receptor for use in treating a disease wherein glucocorticoid treatment is indicated.

The present application also includes a method of reducing a side effect of a glucocorticoid comprising administering, to a subject in need thereof, the glucocorticoid in combination with a therapeutically effective amount of an agent that antagonizes the LXRβ receptor.

The present application further includes a use of an agent that antagonizes the LXRβ receptor for reducing a side effect of a glucocorticoid as well as a use of an agent that antagonizes the LXRβ receptor for preparation of a medicament for reducing a side effect of a glucocorticoid. The application also includes an agent that antagonizes the LXRβ receptor for use to reduce a side effect of a glucocorticoid.

In an embodiment the LXR antagonist is a selective LXRβ antagonist or a combined LXRα/LXRβ antagonist. In a further embodiment the LXR antagonist selectively inhibits LXRβ over LXRα by 1.5 to 10 fold.

In another embodiment the side effect of elevated glucocorticoid levels is selected from one or more of insulin resistance, hyperglycemia, diabetes (for example, steroid diabetes), fatty liver (hepatosteatosis), hypertension, bone loss (for example, osteoporosis), muscle wasting, muscle weakness, increased appetite, weight gain, deposits of fat in the chest, face, upper back and/or stomach, water and/or salt retention leading to swelling and/or edema, high blood pressure, black and blue marks, cataracts, acne, thinning of the skin, stomach ulcers, increased sweating, mood swings, adrenal suppression, adrenal crisis, and psychological problems (for example depression).

In another embodiment of the present application, the side effect of elevated glucocorticoid levels is a gluconeogenic side effect.

In another embodiment, the diseases wherein glucocorticoid treatment is indicated is selected from one or more of rheumatoid arthritis (RA), acute gouty arthritis, osteoarthritis (intra-articular), rheumatic polymyalgia, inflammatory bowel disease (IBD), ulcerative colitis, Crohn's disease, lupus erythematosus, cluster headache prophylaxis, status migrainous, bell's palsy, asthma (acute, chronic and severe exacerbation), COPD (chronic management and exacerbation), allergic rhinitis, sinusitis, croup, post-operative cataracts, conjunctivitis, red eye, nausea/vomiting of pregnancy, hyperthyroidism, hypercalcemia, acne vulgaris, systemic atopic dermatitis, psoriasis, scabies, plantar fasciitis, pruritus (general), sunburn, immunosuppression, immunoglobulin A nephropathy, autoimmune chronic active hepatitis, antenatal, pulmonary cystic fibrosis, cancer, hypercalcemia, post-operations, transplants, alcoholic hepatitis, myelodysplastic syndromes, tuberculosis, bacterial meningitis, drug-induced anaphylaxis, septic shock, intracranial hypertension management and drug-induced aplastic anemia.

In an embodiment of the present application the glucocorticoid is selected from dexamethasone, betamethasone, cortisone, prednisone, prednisolone, methylprednisolone, beclometasone, fludrocortisone, deoxycorticosterone acetate, triamcinolone, and cortisol (hydrocortisone), and pharmaceutically acceptable salts, ester and amide prodrugs and solvates thereof.

The present application also includes the novel compound of the formula:

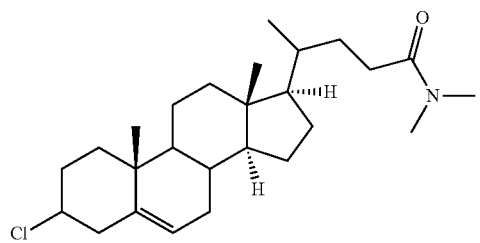 [SMILES: CC(CCC(=O)N(C)C)[C@H]1CC[C@H]2C3CC=C4CC(Cl)CC[C@]4(C)C3CC[C@]12C]

or a pharmaceutically acceptable solvate thereof. This compound is also referred to herein as DMHCl. The present application includes all uses of DMHCl, including its use in diagnostic assays and as a therapeutic.

Other features and advantages of the present application will become apparent from the following detailed description. It should be understood, however, that the detailed description and the specific examples while indicating embodiments of the application are given by way of illustration only. The scope of the claims should not be limited by the embodiments set forth in the examples, but should be given the broadest interpretation consistent with the description as a whole.

BRIEF DESCRIPTION OF THE DRAWINGS

The present application will now be described in greater detail with reference to the drawings in which.

DETAILED DESCRIPTION OF THE APPLICATION

I. Definitions

Figure 1:
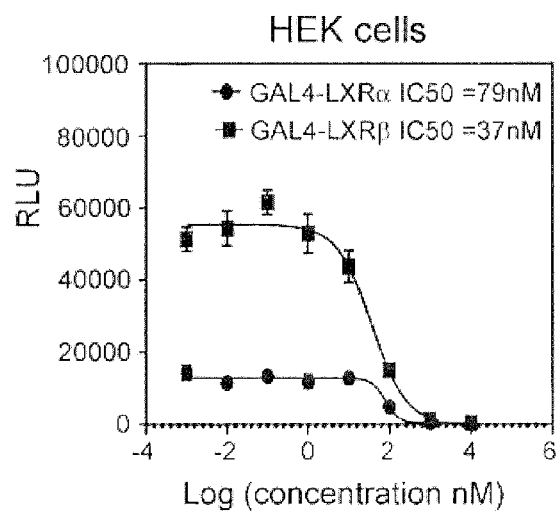
FIG. 1 shows that GSK2033 is a potent LXR antagonist. The selectivity and potency of LXR antagonist GSK2033 was assessed for LXRα and LXRβ in HEK293 cells and in mouse primary hepatocytes. HEK293 cells or mouse primary hepatocytes were co-transfected with GAL4-LXRα, GAL4-LXRβ or GAL4-GR with UAS-luc reporter plasmid. (A) The $IC_{50}$ of GSK2033 against LXRα or LXRβ was determined using an HEK293 cell transfection assay. The dual LXR ligand T0901317 was dosed at the $EC_{80}$ for each receptor (250 nM for GAL4-LXRα and 100 nM for GAL4-LXRβ). (B) GSK2033 did not antagonize the activity of GAL4-GR when activated with 100 nM Dex. (C) The $IC_{50}$ of GSK2033 against LXRα and LXRβ in a mouse primary hepatocyte transfection assay. The dual LXR ligand T0901317 was dosed at the $EC_{80}$ for each receptor (1 μM for GAL4-LXRα and 250 nM for GAL4-LXRβ). (D) GSK2033 did not antagonize the activity of GAL4-GR when activated with 100 nM Dex in primary hepatocytes. Data represent the mean±SD (N=3). $IC_{50}$ values were determined using a sigmoidal curve fit (Prism, GraphPad). RLU=relative luciferase units.
Figure 1:
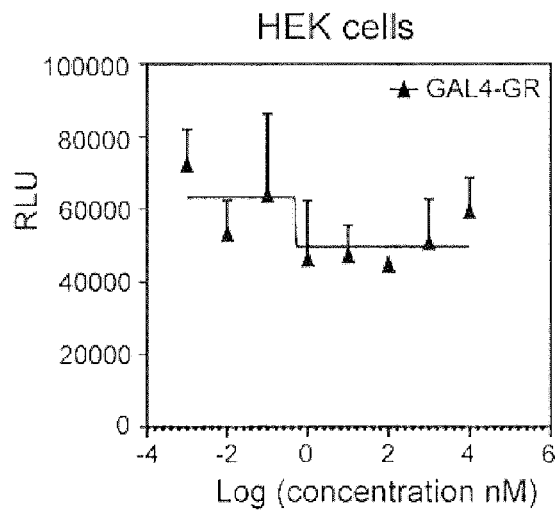
Figure 1:
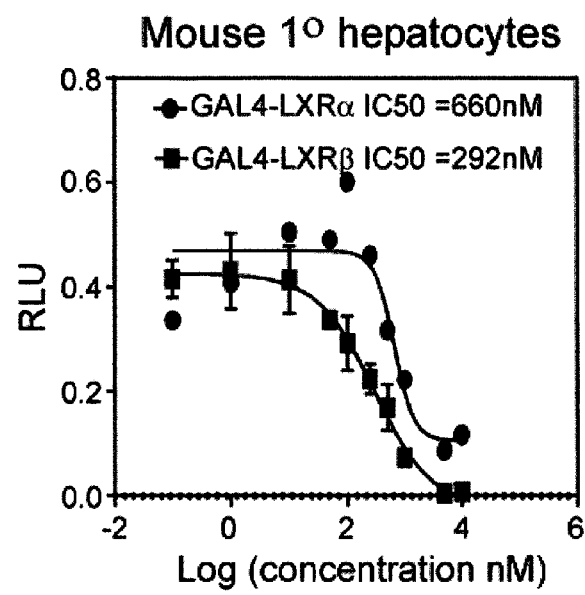
Figure 1:
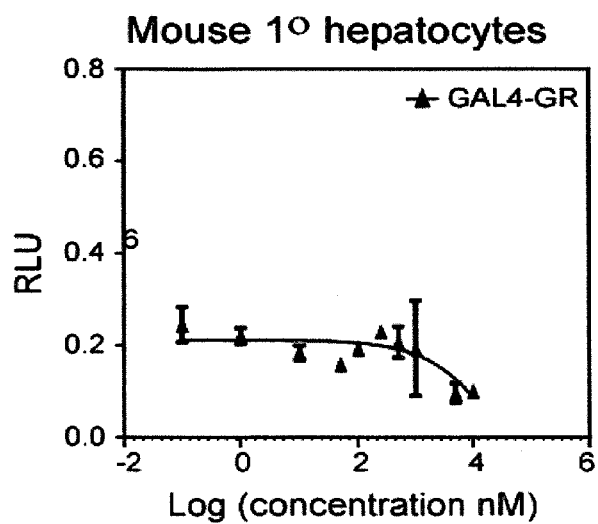

Unless otherwise indicated, the definitions and embodiments described in this and other sections are intended to be applicable to all embodiments and aspects of the application herein described for which they are suitable as would be understood by a person skilled in the art.

As used in this application, the singular forms "a", "an" and "the" include plural references unless the content clearly dictates otherwise. For example, an embodiment including "a glucocorticoid" should be understood to present certain aspects with one glucocorticoid, or two or more additional glucocorticoids.

In embodiments comprising an "additional" or "second" component, such as an additional or second glucocorticoid, the second component as used herein is chemically different from the other components or first component. A "third" component is different from the other, first, and second components, and further enumerated or "additional" components are similarly different.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The term "subject" as used herein includes all members of the animal kingdom including mammals, and suitably refers to humans.

The term "cell" as used herein means a single cell or a plurality of cells.

The term "pharmaceutically acceptable" as used herein means compatible with the treatment of subjects, in particular humans.

The term "pharmaceutically acceptable salt" means an acid addition salt or a basic addition salt of a compound which is suitable for or compatible with the treatment of patients.

The term "pharmaceutically acceptable acid addition salt" as used herein means any non-toxic organic or inorganic salt of any base compound. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, acid addition salts are more soluble in water and various hydrophilic organic solvents, and generally demonstrate higher melting points in comparison to their free base forms. The selection of the appropriate salt will be known to one skilled in the art.

The term "pharmaceutically acceptable basic addition salt" as used herein means any non-toxic organic or inorganic base addition salt of any acid compound. Illustrative inorganic bases which form suitable salts include lithium, sodium, potassium, calcium, magnesium or barium hydroxide. Illustrative organic bases which form suitable salts include aliphatic, alicyclic or aromatic organic amines such as methylamine, trimethylamine and picoline, alkylammonias or ammonia. The selection of the appropriate salt will be known to a person skilled in the art.

The term "ester or amide prodrug" as used herein refers to functional derivatives of a compound which are readily convertible in vivo into the compound from which it is notionally derived. Ester and amide prodrugs are, for example, conventional esters formed with available hydroxy or amino groups, respectively. For example, an available OH or NH group in a compound is acylated using an activated acid in the presence of a base, and optionally, in inert solvent (e.g. an acid chloride in pyridine). Some common esters which have been utilized as prodrugs are phenyl esters, aliphatic ($C_8$-$C_{24}$) esters, acyloxymethyl esters, carbamates and amino acid esters. Conventional procedures for the selection and preparation of suitable ester and amide prodrugs are described, for example, in "Design of Prodrugs" ed. H. Bundgaard, Elsevier, 1985.

The term "treating" or "treatment" as used herein and as is well understood in the art, means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. "Treating" and "treatment" can also mean prolonging survival as compared to expected survival if not receiving treatment. "Treating" and "treatment" as used herein also include prophylactic treatment. For example, a subject can be treated prior to treatment with a glucocorticoid to prevent side effect occurrence or a subject with an early side effect associated with glucocorticoid use can be treated to prevent progression, or alternatively a subject in remission can be treated with a compound or composition described herein to prevent recurrence. Further a person at risk for or suspected of having increased endogenous glucocorticoid levels can be treated to prevent elevation or progress of elevation.

Treatment methods comprise administering to a subject a therapeutically effective amount of an agent that antagonizes the LXRβ receptor, or a therapeutically effective amount of a glucocorticoid in combination with a therapeutically effective amount of an agent that antagonizes the LXRβ receptor. Treatment methods optionally consist of a single administration, or alternatively comprise a series of administrations. For example, the agent that antagonizes the LXRβ receptor or the glucocorticoid in combination with the agent that antagonizes the LXRβ receptor may be administered at least once a week. However, in another embodiment, the agent that antagonizes the LXRβ receptor or the glucocorticoid in combination with the agent that antagonizes the LXRβ receptor may be administered to the subject from about one time per three weeks, or about one time per week to about once daily for a given treatment. In another embodiment, the agent or the glucocorticoid in combination with the agent is administered 2, 3, 4, 5 or 6 times daily.

The length of the treatment period depends on a variety of factors, such as the severity of the disease, the age of the patient, the concentration, the activity of the agent that antagonizes the LXRβ receptor or the glucocorticoid in combination with the agent that antagonizes the LXRβ receptor, and/or a combination thereof. It will also be appreciated that the effective dosage of the agent or the glucocorticoid in combination with the agent used for the treatment or prophylaxis may increase or decrease over the course of a particular treatment or prophylaxis regime. Changes in dosage may result and become apparent by standard diagnostic assays known in the art. In some instances, chronic administration may be required. For example, the agent or the glucocorticoid in combination with the agent is administered to the subject in an amount and for a duration sufficient to treat the patient.

"Palliating" a disease or disorder means that the extent and/or undesirable clinical manifestations of a disorder or a disease state are lessened and/or time course of the progression is slowed or lengthened, as compared to not treating the disorder.

The term "prevention" or "prophylaxis", or synonym thereto, as used herein refers to a reduction in the risk or probability of a subject becoming afflicted with a side effect of elevated glucocorticoid levels or manifesting a symptom of a side effect of elevated glucocorticoid levels.

As used herein, the term "effective amount" or "therapeutically effective amount" means an amount effective, at dosages and for periods of time necessary to achieve the desired result. For example in the context of treating a side effect of elevated glucocorticoid levels, an effective amount is an amount that, for example, reduces the side effect of elevated glucocorticoid levels compared to the side effect of elevated glucocorticoid levels without administration of the agent. Effective amounts may vary according to factors such as the disease state, age, sex and/or weight of the subject. The amount of the agent that antagonizes the LXRβ receptor that will correspond to such an amount will vary depending upon various factors, such as, for example the pharmaceutical formulation, the route of administration, the side effect of elevated glucocorticoid levels, the identity of the subject being treated, the glucocorticoid being used, the condition, disease or disorder the glucocorticoid is being used to treat and the like, but can nevertheless be routinely determined by one skilled in the art.

The term "administered" as used herein means administration of a therapeutically effective dose of an agent or composition of the application to a subject.

The term "side effect" as used herein refers to a biological or therapeutic effect that is secondary to the primary purpose of a therapeutic agent. The side effect is generally undesirable.

The term "elevated glucocorticoid levels" as used herein refers to amounts of glucocorticoid in a cell or subject which are above normal or control levels (i.e. levels in a healthy cell or subject that has not been treated with a glucocorticoid or that does not have a condition, disease or disorder that causes elevated glucocorticoid levels), to an extent that undesirable side effects are manifested. The undesirable side effect is detected either by visual or sensory detection of symptoms or by analysis of a sample from the cell or subject.

The term "LXR antagonist" as used herein refers to any agent that is capable of binding to LXRα and/or LXRβ wherein said binding inhibits or antagonizes the activity of the LXR.

The term "agent that antagonizes the LXRβ receptor" as used herein means any agent that possesses antagonistic activity for the LXRβ receptor. The agent may also have activity at other receptors, as long as such activity is not detrimental to the therapeutic treatment of the subject or cell.

The term "selective antagonist" as used herein refers to a compound that antagonizes LXRα and LXRβ to a greater extent than the other. For example a selective antagonist for LXRβ is a compound that antagonizes LXRβ by 1.5 to 10 fold, 1 to 8 fold, or 2 to 5 fold more than LXRα.

The term "GSK2033" as used herein refers to the compound 2,4,6-trimethyl-N-((3'-(methylsulfonyl)-[1,1'-biphenyl]-4-yl)methyl)-N-((5-(trifluoromethyl)furan-2-yl)methyl)benzenesulfonamide, having the formula:

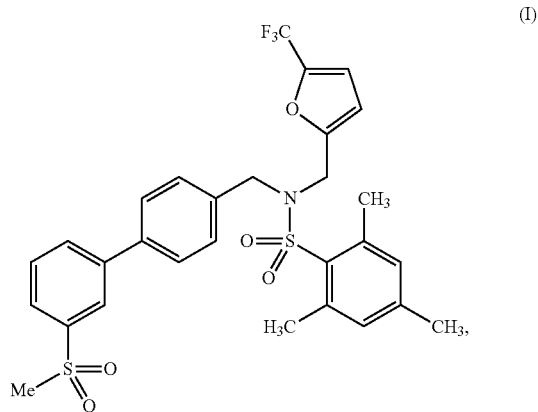 [SMILES: Cc1cc(C)c(S(=O)(=O)N(Cc2ccc(-c3cccc(S(C)(=O)=O)c3)cc2)Cc2ccc(C(F)(F)F)o2)c(C)c1]

or a solvate thereof, in particular, a pharmaceutically acceptable solvate thereof. This compound was reported by Zuercher et al. (2010).[25] It was discovered during a screen for LXR partial agonists.

The term "Amgen54" as used herein refers to a compound having the formula:

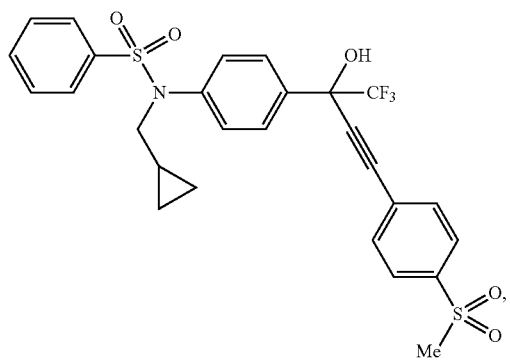 [SMILES: CS(=O)(=O)c1ccc(C#CC(O)(c2ccc(N(CC3CC3)S(=O)(=O)c3ccccc3)cc2)C(F)(F)F)cc1]

or a solvate thereof, in particular, a pharmaceutically acceptable solvate thereof. Amgen54 is an aryl sulfonamide compound disclosed in PCT patent application publication no. WO2003/063576.

The term "DMHCl" as used herein refers to a compound having the formula:

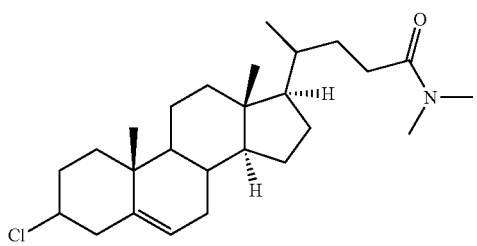 [SMILES: CC(CCC(=O)N(C)C)[C@H]1CC[C@H]2C3CC=C4CC(Cl)CC[C@]4(C)C3CC[C@]12C]

or a solvate thereof, in particular, a pharmaceutically acceptable solvate thereof. In an embodiment, DMHCl is prepared in two steps from 3β-hydroxy-Δ⁵-cholenic acid by conversion of the carboxylic acid to the dimethylamide and displacement of the hydroxyl group by chloride using procedures known in the art, for example as described herein.

The term "gluconeogenic side effect" as used herein refers to a side effect that results in the generation of glucose from carbon sources other than glycogen such as pyruvate, lactate, glycerol, gluconeogenic amino acids and acetyl-CoA.

The term "composition of the application" and the like as used herein means a composition comprising an agent and at least one carrier. In an embodiment, the agent is a pharmaceutically active agent and is formulated into a "pharmaceutical composition of the application" for administration to subjects in a biologically compatible form suitable for administration in vivo.

The term "solvate" as used herein means a compound wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate". The formation of solvates of the compound of the application will vary depending on the solvate. In general, solvates are formed by dissolving the compound in the appropriate solvent and isolating the solvate by cooling or using an antisolvent. The solvate is typically dried or azeotroped under ambient conditions. The selection of suitable conditions to form a particular solvate can be made by a person skilled in the art.

II. Methods and Uses of the Application

In vitro and in vivo studies of the present application have found that pharmacological antagonism of LXRβ can suppress the gluconeogenic side effects associated with GCs without affecting their immunosuppressive properties. For example, studies of the present application using primary hepatocytes and primary macrophages have demonstrated that when agents that antagonize LXRβ are incubated with a glucocorticoid, the induction of gluconeogenic genes in the hepatocytes can be inhibited without altering the immunosuppressive effects of glucocorticoids. It has been shown that co-treatment of glucocorticoids with LXRβ antagonists results in the inhibition of a key gluconeogenic target gene of the GR (Pepck) and decreases glucocorticoid-induced production of glucose in wildtype and LXRα−/− primary hepatocytes. The LXRβ antagonists tested herein have been shown not to affect the anti-inflammatory actions of the glucocorticoids in mouse primary macrophages stimulated with LPS to induce an inflammatory response. Further, a study of LXRα−/− mice treated with a glucocorticoid or a glucocorticoid in combination with an LXRβ antagonist for 5 days showed that plasma glucose levels were significantly decreased in the glucocorticoid+LXRβ antagonist group relative to glucocorticoid treatment alone. In contrast, both groups of mice (glucocorticoid and glucocorticoid+LXRβ antagonist) had significantly smaller spleens compared to vehicle-treated mice, an indication that glucocorticoid-mediated immune suppression was intact. Characterization of liver gene expression found that the increased expression of Pepck (3.7-fold) and FOXO (3.3-fold), both of which are gluconeogenic genes, was significantly dampened in the glucocorticoid+LXRβ antagonist group.

Results of previous studies using knock-out mice lacking LXRβ have suggested that the presence of LXRβ may be detrimental for mediating some of the effects of GCs. However, until the studies in the present application, it was not known whether an LXRβ antagonist could mimic the loss of function effect observed in the LXRβ−/− mice. The ability to predict whether a gene target of LXR will be upregulated or downregulated in the absence of the receptor is not possible due to tissue specific and target gene specific factors such as coactivators and corepressors. For example, in the LXRα/β knock-out mouse, Srebp-1c, a target gene of LXRα/β expressed in the liver is strongly repressed compared to wildtype mice; whereas, Abca1, another target gene of LXRα/β, is significantly de-repressed (increased) in macrophages of LXRα/β knock-out mice compared to wildtype mice.[26] Yet, both genes (Srebp-1c and Abca1) are potently upregulated when wildtype mice are treated with an LXR agonist. In the liver, the Pepck gene is basally elevated (1.5-fold) in the LXRα/β knock-out mice, yet this same gene is suppressed when wildtype mice are treated with an LXR agonist. Based on these data, treatment of WT mice with an LXR antagonist would not have been predicted to cause a decrease in Pepck.

The development of LXR modulators has mainly been restricted to LXR agonists for the treatment of atherosclerosis. Induction of LXR is beneficial for reverse cholesterol transport and for inhibiting inflammation. However, potent LXR agonists have the negative side effect of inducing SREBP-1c, a gene that regulates fatty acid synthesis, and cause, for example, hypertriglyceridemia and fatty liver. LXRβ specific agonists have been targeted for the circumvention of the induction of SREBP-1c as reverse cholesterol transport and inhibition of inflammation can be achieved without activating LXRα, and it is thought that LXRα is primarily responsible for the potent induction of SREBP-1c. Accordingly, prior to the results of the present application, antagonizing LXRβ would not logically have been considered a beneficial therapeutic avenue.

The results of the studies of the present application suggest that surprisingly, the pharmacological antagonism of LXR, in particular, LXRβ can suppress the gluconeogenic side effects of glucocorticoids without affecting the desirable immune suppression. This provides a therapeutic strategy to maintain the immunosuppressive effects of glucocorticoids substantially devoid of side effects associated with steroid use. There are no combination treatments or glucocorticoids presently on the market that meet this need, and prior to the results of the present application, the application of LXR antagonists to this condition could not have been predicted. Further, the side effects caused by elevated endogenous glucocorticoid levels, such as elevated glucocorticoid levels that result from the presence of a condition, disease or disorder, for example Cushing's syndrome, are also treatable via pharmacological antagonism of LXR, in particular, LXRβ.

Accordingly, the present application includes a method of treating a side effect of elevated glucocorticoid levels comprising administering a therapeutically effective amount of an agent that antagonizes the LXRβ receptor to a subject in need thereof.

The present application further includes a use of an agent that antagonizes the LXRβ receptor for treating a side effect of elevated glucocorticoid levels as well as a use of an agent that antagonizes the LXRβ receptor for preparation of a medicament for treating a side effect of elevated glucocorticoid levels. The application also includes an agent that antagonizes the LXRβ receptor for use in treating a side effect of elevated glucocorticoid levels.

In one embodiment, the elevated glucocorticoid levels are the result of elevated endogenous glucocorticoid levels, such as elevated glucocorticoid levels that result from the presence of a condition, disease or disorder, for example Cushing's syndrome, type 2 diabetes and chronic stress.

In another embodiment, the elevated glucocorticoid levels are the result of elevated exogenous glucocorticoid levels, such as elevated glucocorticoid levels that result from administration of a glucocorticoid as a therapeutic agent.

In one of its embodiments, the present application includes a method of treating a disease wherein glucocorticoid treatment is indicated comprising administering a therapeutically effective amount of a glucocorticoid in combination with a therapeutically effective amount of an agent that antagonizes the LXRβ receptor to a subject in need thereof.

The present application further includes a use of a glucocorticoid in combination with an agent that antagonizes the LXRβ receptor for treating a disease wherein glucocorticoid treatment is indicated, as well as a use of a glucocorticoid in combination with an agent that antagonizes the LXRβ receptor for preparation of a medicament for treating a disease wherein glucocorticoid treatment is indicated. The application also includes a glucocorticoid in combination with an agent that antagonizes the LXRβ receptor for use in treating a disease wherein glucocorticoid treatment is indicated.

In another of its embodiments, the present application includes a method of reducing a side effect of a glucocorticoid comprising administering, to a subject in need thereof, the glucocorticoid in combination with a therapeutically effective amount of an agent that antagonizes the LXRβ receptor.

The present application further includes a use of an agent that antagonizes the LXRβ receptor for reducing a side effect of a glucocorticoid as well as a use of an agent that antagonizes the LXRβ receptor for preparation of a medicament for reducing a side effect of a glucocorticoid. The application also includes an agent that antagonizes the LXRβ receptor for use to reduce a side effect of a glucocorticoid.

In an embodiment the agent that antagonizes the LXRβ receptor is a selective LXRβ antagonist or a combined LXRα/LXRβ antagonist. In a further embodiment the LXR antagonist selectively inhibits LXRβ over LXRα by 1.5 to 10 fold, 1 to 8 fold, or 2 to 5 fold.

In an embodiment of the application the agent that antagonizes the LXRβ receptor is any agent that binds to LXRβ wherein said binding inhibits or antagonizes the activity of the LXRβ. In an embodiment the agent has an $IC_{50}$ for the LXRβ receptor of 0.01 nM to 10 μM, 0.1 nM to 1 μM or 1 nM to 1 μM. In another embodiment the agent has an $IC_{50}$ for the LXRβ receptor of 0.01 nM to 1 μM, 0.1 nM to 1 μM or 1 nM to 0.5 μM.

In an embodiment, the agent that antagonizes the LXRβ receptor is any agent that antagonizes the LXRβ receptor at levels that result in a measurable therapeutic effect, that is, a side effect of elevated glucocorticoid levels is reduced, compared to a control, by an amount that is statistically significant. Here a control is a subject or cell that has been treated under the same conditions, except without the agent that antagonizes the LXRβ receptor. In a further embodiment, the agent that antagonizes the LXRβ receptor is selected from a compound, an antisense nucleic acid or an antibody. In yet another embodiment, the agent that antagonizes the LXRβ receptor is a compound selected from the group consisting of GSK2033, Amgen54 and DMHCl, and pharmaceutically acceptable solvates thereof.

In an embodiment of the present application the glucocorticoid is selected from dexamethasone, betamethasone, cortisone, prednisone, prednisolone, methylprednisolone, beclometasone, fludrocortisone, deoxycorticosterone acetate, triamcinolone, and cortisol (hydrocortisone) and pharmaceutically acceptable salts, ester and amide prodrugs and solvates thereof. In another embodiment of the present application the glucocorticoid is selected from dexamethasone, hydrocortisone, prednisone and triamcinolone acetonide. In yet another embodiment, the glucocorticoid is dexamethasone.

It is an embodiment of the present application that the side effect of elevated glucocorticoid levels is selected from one or more of insulin resistance, hyperglycemia, diabetes (for example, steroid diabetes), fatty liver (hepatosteatosis), hypertension, bone loss (for example, osteoporosis), muscle wasting, muscle weakness, increased appetite, weight gain, deposits of fat in the chest, face, upper back and/or stomach, water and/or salt retention leading to swelling and/or edema, high blood pressure, black and blue marks, cataracts, acne, thinning of the skin, stomach ulcers, increased sweating, mood swings, adrenal suppression, adrenal crisis, and psychological problems (for example depression).

In another embodiment of the present application, the side effect of elevated glucocorticoid levels is a gluconeogenic side effect, for example, hyperglycemia and hepatosteatosis.

In another embodiment, the disease wherein glucocorticoid treatment is indicated is selected from one or more of rheumatoid arthritis (RA), acute gouty arthritis, osteoarthritis (intra-articular), rheumatic polymyalgia, inflammatory bowel disease (IBD), ulcerative colitis, Crohn's disease, lupus erythematosus, cluster headache prophylaxis, status migrainous, bell's palsy, asthma (acute, chronic and severe exacerbation), COPD (chronic management and exacerbation), allergic rhinitis, sinusitis, croup, post-operative cataracts, conjunctivitis, red eye, nausea/vomiting of pregnancy, hyperthyroidism, hypercalcemia, acne vulgaris, systemic atopic dermatitis, psoriasis, scabies, plantar fasciitis, pruritis (general), sunburn, immunosuppression, immunoglobulin A nephropathy, autoimmune chronic active hepatitis, antenatal, pulmonary cystic fibrosis, cancer, hypercalcemia, post-operations, transplants, alcoholic hepatitis, myelodysplastic syndromes, tuberculosis, bacterial meningitis, drug-induced anaphylaxis, septic shock, intracranial hypertension management and drug-induced aplastic anemia. In another embodiment, the disease is selected from those wherein long term glucocorticoid administration is needed.

It is an embodiment of the present application that the agent that antagonizes the LXRβ receptor is administered contemporaneously with the glucocorticoid. As used herein, "contemporaneous administration" of two substances to a subject means providing each of the two substances so that they are both biologically active in the individual at the same time. The exact details of the administration will depend on the pharmacokinetics of the two substances in the presence of each other, and can include administering the two substances within a few hours of each other, or even administering one substance within 24 hours of administration of the other, if the pharmacokinetics are suitable. Design of suitable dosing regimens is routine for one skilled in the art. In particular embodiments, two substances will be administered substantially simultaneously, i.e., within minutes of each other, or in a single composition that contains both substances.

It is a further embodiment of the present application that the agent that antagonizes the LXRβ receptor and the glucocorticoid are administered to a subject in a non-contemporaneous fashion.

The active agents, including the agent that antagonizes the LXRβ receptor and/or glucocorticoid, are suitably formulated into pharmaceutical compositions for administration to subjects in a biologically compatible form suitable for administration in vivo.

The active agents (i.e. agent that antagonizes the LXRβ receptor and/or glucocorticoid) are administered to a subject in a variety of forms depending on the selected route of administration, as will be understood by those skilled in the art. For example, an active agent is administered, by oral, parenteral, buccal, sublingual, nasal, rectal, patch, pump or transdermal administration and the pharmaceutical compositions formulated accordingly. Conventional procedures and ingredients for the selection and preparation of suitable compositions are described, for example, in Remington's Pharmaceutical Sciences (2000—20th edition) and in The United States Pharmacopeia: The National Formulary (USP 24 NF19) published in 1999.

In an embodiment, an active agent is orally administered, for example, with an inert diluent or with an assimilable edible carrier, or it is enclosed in hard or soft shell gelatin capsules, or it is compressed into tablets, or it is incorporated directly with the food of the diet. For oral therapeutic administration, the agent is incorporated with excipient and used in the form of ingestible tablets, buccal tablets, troches, capsules, elixirs, suspensions, syrups, wafers, and the like. Oral dosage forms also include modified release, for example immediate release and timed-release, formulations. Examples of modified-release formulations include, for example, sustained-release (SR), extended-release (ER, XR, or XL), time-release or timed-release, controlled-release (CR), or continuous-release (CR or Contin), employed, for example, in the form of a coated tablet, an osmotic delivery device, a coated capsule, a microencapsulated microsphere, an agglomerated particle, e.g., as of molecular sieving type particles, or, a fine hollow permeable fiber bundle, or chopped hollow permeable fibers, agglomerated or held in a fibrous packet. In an embodiment, timed-release compositions are formulated, e.g. liposomes or those wherein the active agent is protected with differentially degradable coatings, such as by microencapsulation, multiple coatings, etc. Liposome delivery systems, include, for example, small unilamellar vesicles, large unilamellar vesicles and multilamellar vesicles. Liposomes are, for example, formed from a variety of phospholipids, such as cholesterol, stearylamine or phosphatidylcholines.

It is also possible to freeze-dry the active agent and use the lyophilizates obtained, for example, for the preparation of products for injection.

In a further embodiment, an active agent is administered parenterally. Parenteral administration includes intravenous, intraperitoneal, subcutaneous, intramuscular, transepithelial, nasal, intrapulmonary, intrathecal, rectal and topical modes of administration. In an embodiment, parenteral administration is by continuous infusion over a selected period of time. Solutions of the agent are, for example, prepared in water suitably mixed with a surfactant such as hydroxypropylcellulose. In another embodiment, dispersions are prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists.

In an embodiment, compositions for nasal administration are conveniently formulated as aerosols, drops, gels or powders. Aerosol formulations typically comprise a solution or fine suspension of the active agent in a physiologically acceptable aqueous or non-aqueous solvent and are usually presented in single or multidose quantities in sterile form in a sealed container, which can take the form of a cartridge or refill for use with an atomising device. Alternatively, the sealed container is a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. In a further embodiment, the aerosol dosage forms also take the form of a pump-atomizer.

Compositions suitable for buccal or sublingual administration include tablets, lozenges, and pastilles, wherein the active agent is formulated with a carrier such as sugar, acacia, tragacanth, or gelatin and glycerine. Compositions for rectal administration are conveniently in the form of suppositories containing a conventional suppository base such as cocoa butter.

In an embodiment, an active agent is delivered by the use of monoclonal antibodies as individual carriers to which the agent molecules are coupled. In a further embodiment, an active agent is coupled with soluble polymers as targetable drug carriers. Such polymers include, for example, polyvinylpyrrolidone, pyran copolymer, polyhydroxypropylmethacrylamide-phenol, polyhydroxy-ethylaspartamide-phenol, and polyethyleneoxide-polylysine substituted with palmitoyl residues. In a further embodiment, the active agent is coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels. In a still further embodiment, an active agent is delivered by the use of nanoparticles.

The dosage of an active agent can vary depending on many factors such as the pharmacokinetic properties of the agent, the mode of administration, the age, health and weight of the recipient, the nature and extent of the symptoms, the frequency of the treatment and the type of concurrent treatment, if any, and the clearance rate of the agent in the subject to be treated. One of skill in the art can determine the appropriate dosage based on the above factors. The active agent(s) may be administered initially in a suitable dosage that may be adjusted as required, depending on the clinical response.

The dosage of the glucocorticoid, if present, will depend on the condition being treated and will be an amount that is known in the art to be prescribed for the treatment of that condition. Such information is readily available to a person skilled in the art. It is an embodiment that the glucocorticoid is administered orally, by injection, intravenously or by inhalation.

As a representative example, oral dosages of an agent that antagonizes the LXRβ receptor range between about 1 mg per day to about 1000 mg per day for an adult, suitably about 1 mg per day to about 500 mg per day, more suitably about 1 mg per day to about 250 mg per day. In an embodiment of the application, compositions are formulated for oral administration and the agent that antagonizes the LXRβ receptor is suitably in the form of tablets containing 0.25, 0.5, 0.75, 1.0, 5.0, 10.0, 20.0, 25.0, 30.0, 40.0, 50.0, 60.0, 70.0, 75.0, 80.0, 90.0, 100.0, 150, 200, 250, 300, 350, 400, 450, 500, 550, 600, 650, 700, 750, 800, 850, 900, 950 or 1000 mg of active agent per tablet. In an embodiment, the agent that antagonizes the LXRβ receptor is administered in a single daily dose or the total daily dose may be divided into two, three or four daily doses.

The present application also includes a pharmaceutical package or kit comprising an agent that antagonizes the LXRβ receptor and instructions for use in treating a side effect of elevated glucocorticoid levels or for use in combination with a glucocorticoid for treating a disease wherein glucocorticoid treatment is indicated. In an embodiment, the pharmaceutical package or kit further includes the glucocorticoid. In a further embodiment, the agent that antagonizes the LXRβ receptor and glucocorticoid are formulated as pharmaceutical compositions. The pharmaceutical compositions for the agent that antagonizes the LXRβ receptor and the glucocorticoid may be formulated for delivery by the same route or by different routes using the methods described above.

The following non-limiting examples are illustrative of the present application:

EXAMPLES

Example 1

In Vitro Studies to Determine LXR Isoform Specific Potency of GSK2033

In a preliminary experiment of the present study, it was shown using HEK293 cells that basal repression of LXRα and LXRβ by GSK2033 treatment occurred at 3 doses, but the $IC_{50}$ for each of the LXR isoforms was not determined at that time.

Further experiments were then carried out to determine the inhibitory potencies for the individual LXR isoforms in HEK 293 cells by co-transfecting UAS-reporter and GAL4-LBD of the nuclear receptors LXRα, LXRβ and GR and then treating with 8 different concentrations of GSK2033. To assess suppression of ligand activated receptors, the transfected cells were co-treated with increasing doses of GSK2033, in addition to T09091317 or Dex (dexamethasone) (at $EC_{80}$ of LXR isoforms and GR, respectively).

The $IC_{50}$ values for GSK2033 were found to be 79 nM and 37 nM for LXRα and LXRβ, respectively (FIG. 1A); and Dex induced GR activity was unaffected by GSK2033 (FIG. 1B).

Next, a similar test of GSK2033 inhibitory potency was performed in wildtype (WT) mouse primary hepatocytes, where the $IC_{50}$ values for each of the LXR isoforms were right-shifted almost 10-fold ($IC_{50}$ LXRα 660 nM and $IC_{50}$ LXRβ 292 nM) (FIG. 1C). GR activity remained unaffected by GSK2033 in the primary hepatocytes (FIG. 1D).

Example 2

Studies in Mouse Primary Macrophages to Investigate Immunogenic Effects of Dex±GSK2033 Treatment Immune suppression is a desired therapeutic effect of GC drugs presently on the market. Activation of GR by a GC represses the expression of genes important for inducing inflammation at the same time increasing the expression of genes involved in the anti-inflammatory response.

To assess the ability of GSK2033 to affect GR-mediated inflammatory suppression, a number of gene expression studies were conducted on primary macrophages isolated from WT, LXRα-/- and LXRβ-/- mice. Cells were pre-treated with 10 ng/ml lipopolysaccharide (LPS) for 6 hrs (to induce a potent inflammatory response) followed by treatment of 100 nM Dex, 10 μM GSK2033 and/or 250 nM T09 for 18 hrs.

Figure 2:
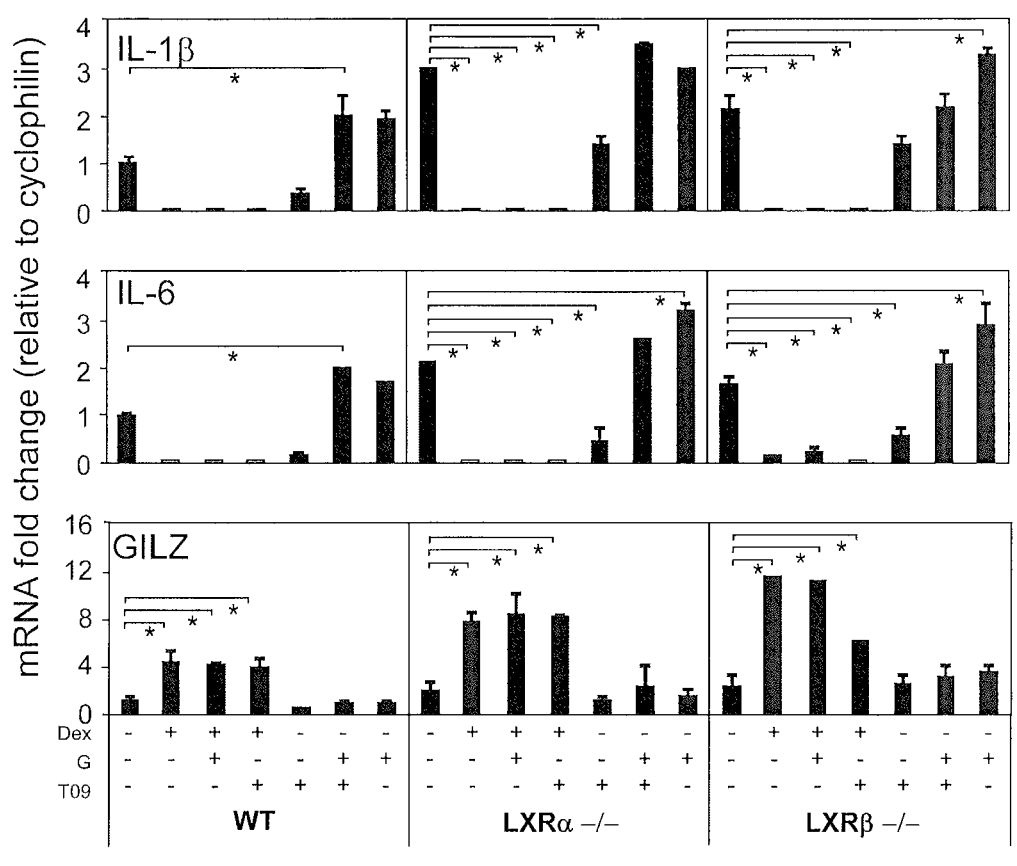
FIG. 2 shows that GR-mediated immune suppression is not affected by GSK2033 co-treatment in mouse primary macrophages. The expression of genes involved in immune response IL-1β, IL-6 and GILZ was measured following an overnight treatment with Dex 100 nM, 250 nM T0901317 (T09), and/or 10 μM GSK2033 in LPS activated WT, LXR α –/– and LXRβ –/– mouse primary macrophages, by RT-QPCR. Data represent the Avg±SD, N=3. *P<0.05 by One way ANOVA, Student Newman Keuls.

The gene expression results from the WT, LXRα-/- and LXRβ-/- primary macrophages showed that Dex-mediated IL-1β and IL-6 repression is unaffected by GSK2033 co-treatment (FIG. 2). Moreover, GR-mediated induction of the anti-inflammatory gene GILZ (Glucocorticoid-induced leucine zipper) is unaffected by GSK2033 co-treatment (FIG. 2 bottom panel). LXR agonist (T09) mediated suppression of IL-1β and IL-6 was also observed, which was antagonized by GSK2033 co-treatment (FIG. 2).

These gene expression results from the mouse primary macrophages suggest that antagonizing LXR activity by GSK2033 does not alter the ability of GR to suppress inflammation.

Example 3

Studies in Mouse Primary Hepatocytes to Investigate the Gluconeogenic Effects of Dex±GSK2033 Treatment A major undesirable side effect of GC treatment is increased glucose production by the liver. To investigate whether antagonism of LXRs along with Dex treatment alters GR-mediated Pepck expression and glucose production in vitro, a number of gene expression and glucose production studies were conducted on mouse primary hepatocytes isolated from WT, LXRα-/- and LXRβ-/- mice.

Figure 3:
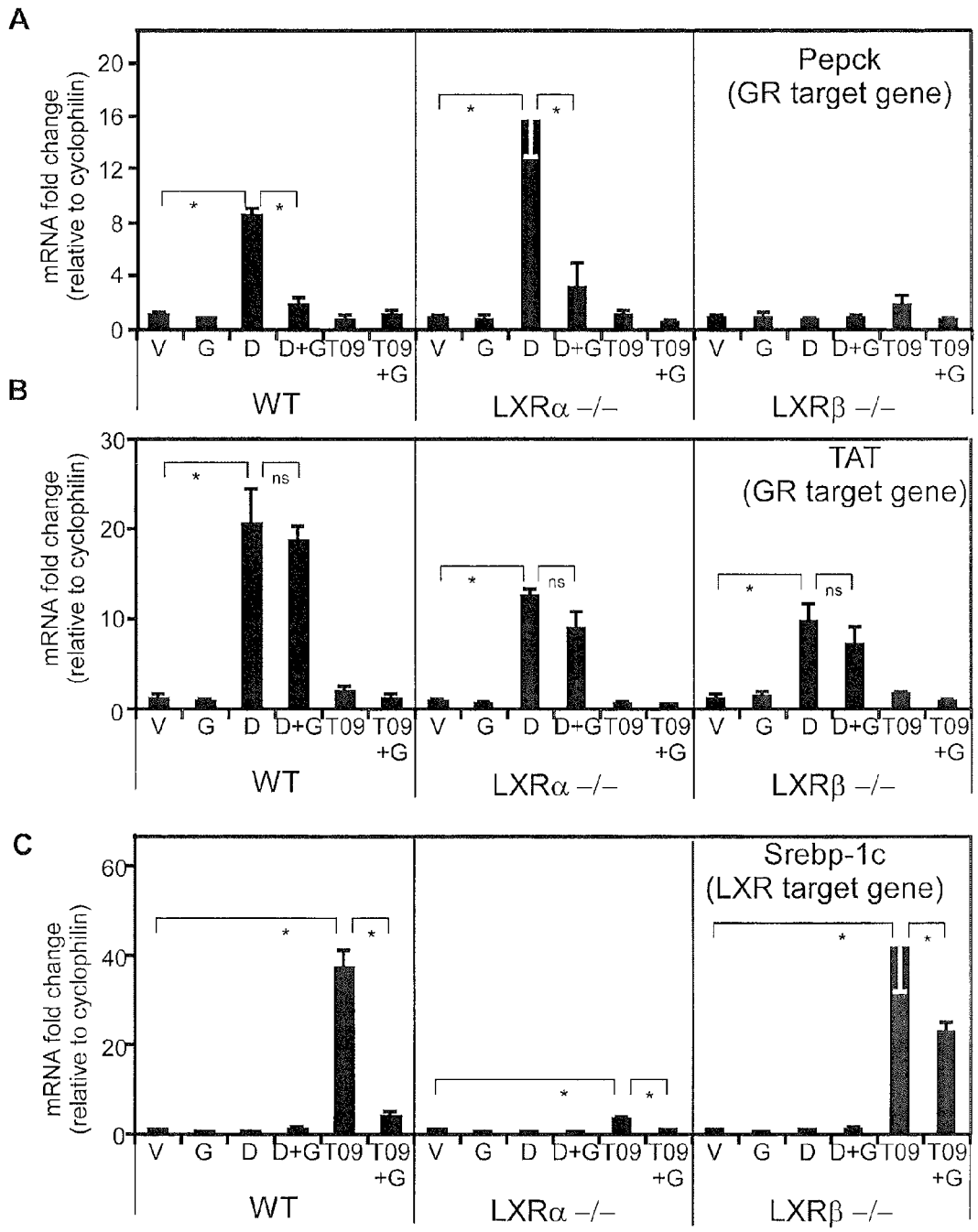
FIG. 3 shows that co-treatment of Dex with GSK2033 results in repression of gluconeogenic gene expression and glucose production in mouse primary hepatocytes. Expression of (A) Pepck (gluconeogenic GR target gene); (B) TAT (GR target gene); and (C) Srebp-1c (LXR target gene) expression in WT, LXRα–/– and LXRβ–/– mouse primary hepatocytes following 18 hr treatment with Veh, 10 μM GSK2033, 250 nM T09, 100 nM Dex alone or in combination. T09 treatment was used as a positive control for LXR activity. (D) Glucose output over 24 hrs from LXRα–/– and LXRβ–/– mouse primary hepatocytes following Dex 100 nM±10 μM GSK2033 treatment. (E) Glucose output over 8 hrs from WT hepatocytes following Dex 500 nM±10 μM GSK2033 treatments. Data represent the Avg±SD, N=3. *P<0.05 by One way ANOVA, Student Newman Keuls. Legend: V=vehicle, G=GSK2033 (LXR antagonist); D=dexamethasone (GR agonist); and T09=T0901317 (LXR agonist).
Figure 3:
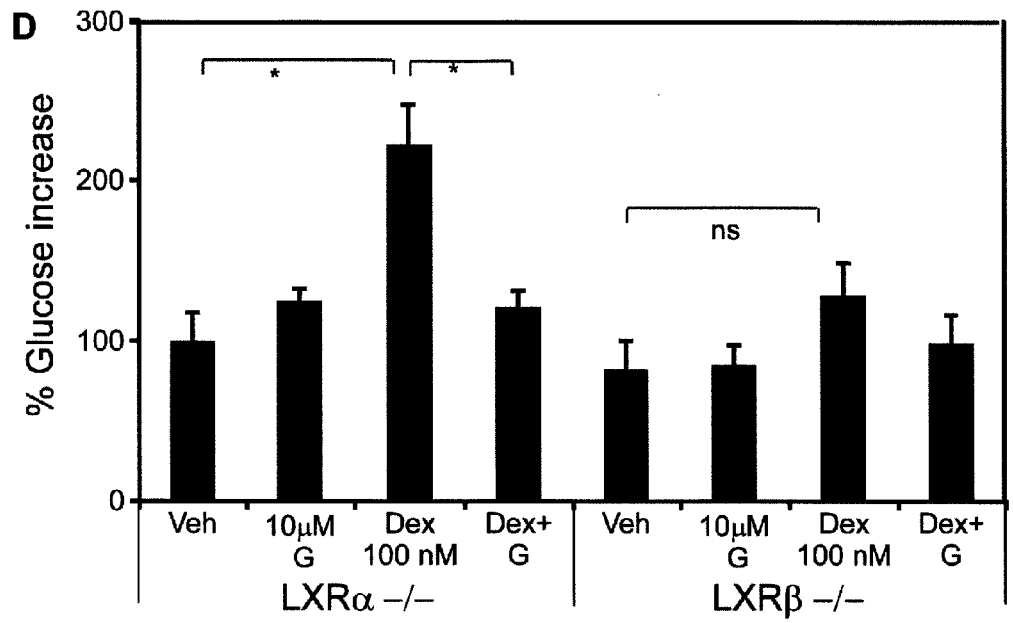
Figure 3:
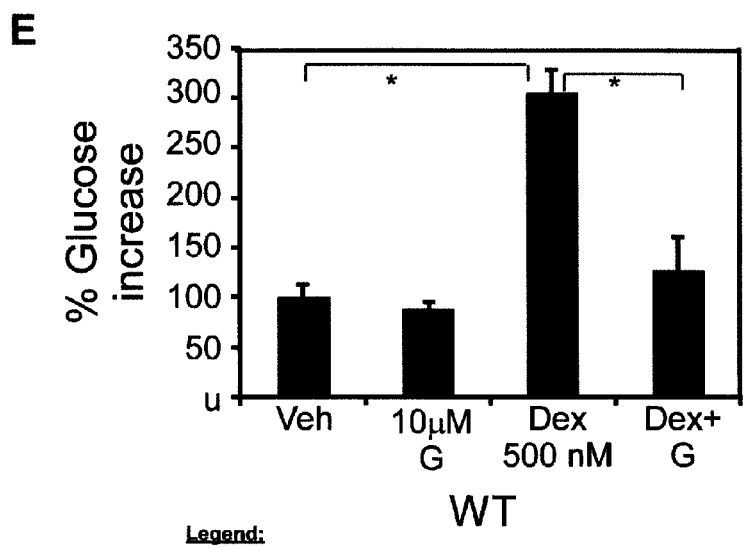

For the gene expression studies, the isolated hepatocytes were cultured at least 24 hrs prior to treatment with 100 nM Dex, 10 μM GSK2033 and/or 250 nM T09 overnight, and then harvested to isolate mRNA. Dex-induced Pepck expression was significantly down-regulated by GSK2033 co-treatment in both WT (from 8.5 fold to 1.9 fold) and LXRα-/- (from 15.7 fold to 3.2 fold) primary hepatocytes (FIG. 3A). Dex treatment did not increase Pepck expression in LXRβ-/- primary hepatocytes, which remained unchanged with GSK2033 co-treatment (FIG. 3A).

In contrast to Pepck, the expression of tyrosine aminotransferase (TAT), a non-gluconeogenic GR target gene, was induced significantly in each of the WT (20.8 fold), LXRα-/- (12.7 fold) and LXRβ-/- (9.7 fold) hepatocytes and this induction by was not altered by GSK2033 co-treatment (FIG. 3B).

The LXR target gene Srebp-1c was induced by the LXR agonist T09, in each of the WT (from 37.7 fold), LXRα-/- (3.7 fold) and LXRβ-/- (42.0 fold) hepatocytes, and this induction was significantly decreased by GSK2033 co-treatment (FIG. 3C).

Initial glucose production studies were performed on LXRα-/- and LXRβ-/- primary hepatocytes treated with 100 nM Dex±10 µM GSK2033 for 24 hours in glucose production media. Only LXRα-/- primary hepatocytes were able to secrete significant glucose (2.2 fold) in response to Dex treatment and this was significantly hampered by GSK2033 co-treatment (1.2 fold) (FIG. 3D). While not wishing to be limited by theory, subsequent to conducting these initial studies it was realized that 24 hour incubation of hepatocytes in gluconeogenic media may be too long. In the literature, for this type of assay, primary heptocytes are usually incubated up to 12 hours. As such, for subsequent studies of the present application, WT cells were treated with 500 nM Dex for 8 hours to be able to measure detectable levels of glucose in the media.

In response to Dex treatment, WT hepatocytes secreted significantly more glucose (3-fold). Remarkably, glucose secretion in the WT hepatocytes was also significantly inhibited by GSK2033 treatment (1.25-fold) (FIG. 3E). This was significant because the selectivity of GSK2033 for LXRβ vs. LXRα is only 2.5-fold higher in hepatocytes.

The results from these glucose production experiments suggest that GSK2033 co-treatment with Dex significantly reverses the glycemic side effects associated with GR activity.

Example 4

In Vivo Studies with GSK2033 Co-treatment with Dex

Having observed promising results with GSK2033 co-treatment with Dex in-vitro (GSK2033-mediated suppression of GC-induced gluconeogenic side effects without affecting desirable immune suppression); a study was conducted, in which whole body LXRα-/- mice were treated with vehicle (Veh), 2.5 mg/kg bid (subcutaneous injection) Dex or Dex+40 mg/kg GSK2033 (once a day intraperitoneal injection) for 5 days, and sacrificed at lights on.

Figure 4:
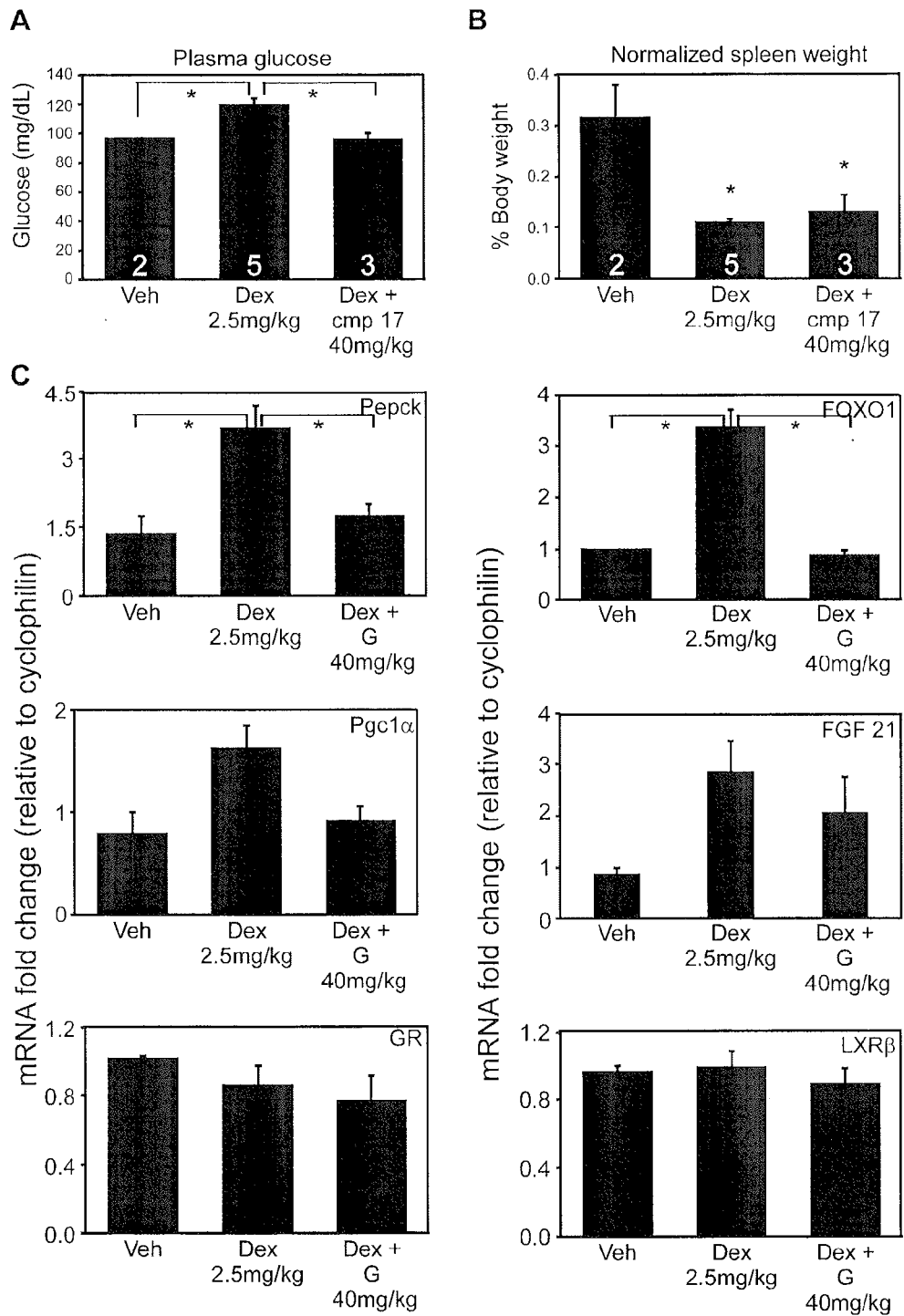
FIG. 4 shows that co-treatment of Dex with GSK2033 results in repression of gluconeogenic gene expression and glucose production without affecting immune suppression in LXRα–/– mice. LXRα–/– mice were treated with Vehicle (Veh), Dex (2.5 mg/kg) b.i.d. or GSK2033 40 mg/kg (once a day) along with Dex b.i.d. for 5 days. (A) Plasma glucose levels were measured by a colorimetric kit (Wako). (B) Spleen weights were measured at the time of sacrifice, and are presented normalized to body weight. (C) Liver Pepck, FOXO1, Pgc 1α, FGF21, GR and LXRβ gene expression measured by QPCR. Data represent the Avg±SEM, N=2-5. *P<0.05 by One way ANOVA, Student Newman Keuls.

Plasma analysis of the study showed that the mice in the Dex group had significantly higher glucose than the mice in Veh or Dex+GSK2033 groups, and mice in the Dex+GSK2033 treatment group had similar plasma glucose levels as the Veh group (FIG. 4A).

Spleen atrophy is a measure of GC-mediated immune suppression. Mice in both the Dex and Dex+GSK2033 treatment group had significantly smaller spleens compared to the mice treated with Veh (FIG. 4B).

Liver gene expression analysis showed gluconeogenic genes Pepck (3.7-fold) and FOXO 1 (3.3-fold) were significantly induced in the livers of mice in the Dex group and this induction was normalized in the livers of mice in Dex+GSK2033 group (FIG. 4C). Other gluconeogenic genes PGC1α and FGF21 also showed trends of increased expression in Dex group compared to Veh and Dex+GSK2033 group. Moreover, expression of the nuclear receptors GR and LXR did not change across the treatment groups (FIG. 4C).

Results from this study suggest that pharmacological antagonism of LXRβ can suppress gluconeogenic side effects associated with GCs without affecting the desired immune suppression in mice.

Example 5

Preparation of DMHCl

3β-Hydroxy-$\Delta^5$-cholenic acid was converted to its dimethyl amide by treating a solution of the acid in dichloromethane with 1.1 equivalents of freshly distilled triethyl amine followed by addition of 1.1 equivalents of ethyl chloroformate. The resulting reaction mixture was stirred for two hours at ambient temperature. 3.0 equivalents of freshly distilled triethylamine and 2.0 equivalents of dimethylammonium hydrochloride were then added, in that order, and the resulting reaction mixture was stirred at ambient temperature for approximately 16 hours. Isolation of the crude product was accomplished by dilution of the reaction mixture with ethyl acetate, and washing with 1M HCl aqueous solution. The organic layer thus obtained was washed with a saturated aqueous NaCl solution and dried with $MgSO_4$. Removal of the solvent using a rotary evaporator provided the crude material used in the next step. The hydroxyl group was converted to the corresponding chloride by treating a dichloromethane solution of the dimethyl amide prepared in the previous step with 4.0 equivalents of thionyl chloride and allowing the resulting reaction mixture to stir at ambient temperature for approximately 16 hours. Isolation of the product was achieved by dilution of the reaction mixture with ethyl acetate and washing with a saturated aqueous solution of $NaHCO_3$. The organic layer thus obtained was washed with a saturated aqueous NaCl solution and dried with $MgSO_4$. Purification of the final product was achieved by recrystallization from ethyl acetate.

Example 6

Further Studies in Mouse Primary Hepatocytes to Investigate Gluconoeogenic Effects of GC's±GSK 2033

To investigate whether antagonism of LXRs along with other GC's alters GR-mediated gluconeogenic gene expression (Pepck and G6Pc) in vitro, a number of gene expression studies were conducted on mouse primary hepatocytes isolated from LXRα-/- mice.

Figure 5:
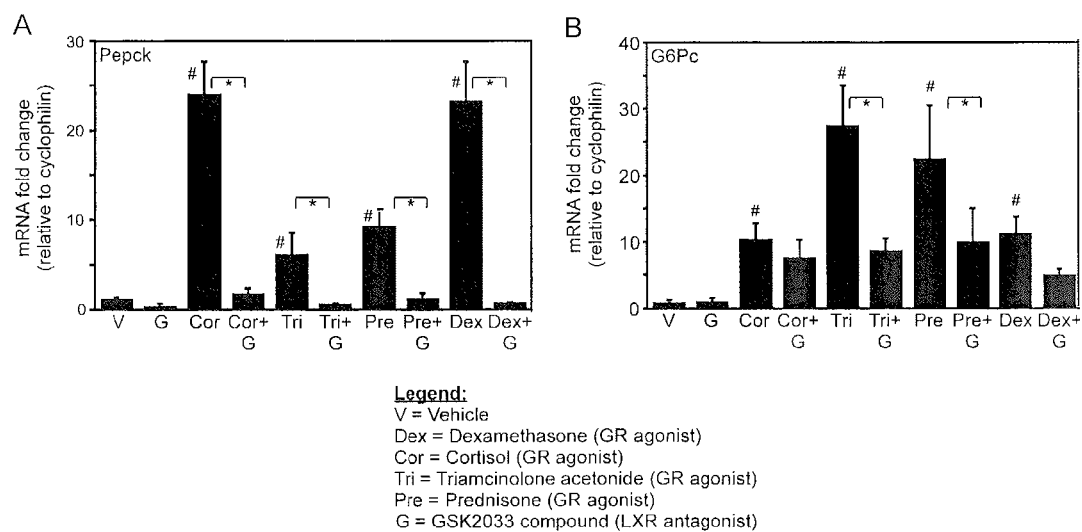
FIG. 5 shows that GSK2033 results in the repression of gluconeogenic gene expression when treated with a variety of different glucocorticoids. Pepck (FIG. 5A) and G6Pc (FIG. 5B) gene expression in LXRα–/– mouse primary hepatocytes treated with combinations of different GC compounds 100 nM Dex, 10 μM cortisol (hydrocortisone), 10 μM prednisone and 10 μM triamcinolone acetonide±10 μM GSK2033, compared with controls. Data is the average±SD (n=3). #P<0.05 relative to vehicle treatment; *P<0.05 relative to GC treatment alone. One way ANOVA, Student Newman Keuls.

For the gene expression studies, the isolated hepatocytes were cultured at least 24 hrs prior to treatment with 10 µM Cortisol, 10 µM Triamcinolone acetonide, 10 µM Prednisone, and 100 nM Dex all±10 µM GSK2033 overnight, and then harvested to isolate mRNA. GC-induced Pepck expression was significantly decreased by GSK2033 co-treatment in LXRα-/- primary hepatocytes (Cortisol: 23.9 fold to 1.7 fold, Triamcinolone acetonide: 6.1 fold to 0.6 fold; Prednisone: 9.3 fold to 1.24 fold; and Dex: 23.2 fold to 0.8 fold) (FIG. 5A). Furthermore, GC-induced G6Pc expression was also dampened by GSK2033 co-treatment in LXRα-/- primary hepatocytes (Cortisol: 10.3 fold to 7.5 fold, Triamcinolone acetonide: 27.3 fold to 8.6 fold; Prednisone from 22.3 fold to 9.8 fold, and Dex from 11.2 fold to 4.9 fold) (FIG. 5B).

Example 7

In Vitro Studies to Determine LXR Isoform Specific Potency of the LXR Antagonists GSK2033, Amgen 54 and DMHCl A number of experiments were carried out to determine the relative inhibitory potencies of GSK2033, Amgen 54 and DMHCl for the individual LXR isoforms in HEK 293 cells by co-transfecting UAS-reporter and GAL4-LBD of the nuclear receptors LXRα, LXRβ and GR and then treating with 6 different concentrations of GSK2033, Amgen 54 and DMHCl. To assess suppression of ligand activated receptors, the transfected cells were co-treated with increasing doses of GSK2033, Amgen 54 and DMHCl, in addition to T09091317 or Dex (at $EC_{80}$ of LXR isoforms and GR, respectively).

Figure 6:
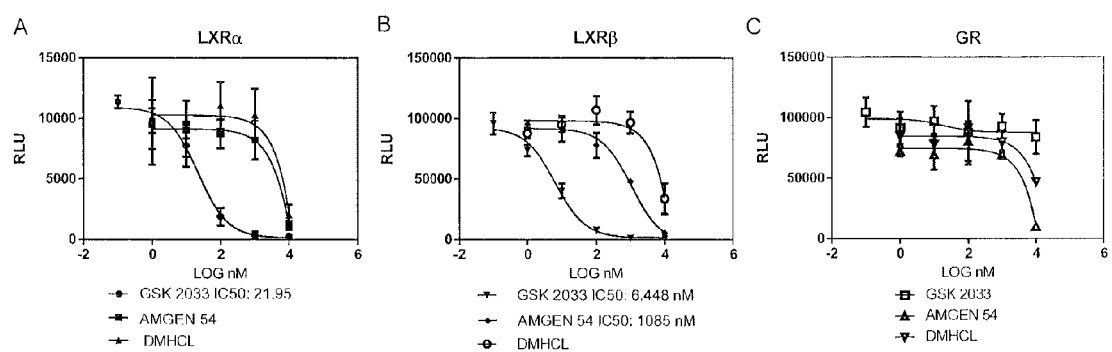
FIG. 6 shows that GSK2033, Amgen54 and DMHCl are all LXR antagonists. The selectivity and potency of each of these LXR antagonists was assessed for LXRα and LXRβ in HEK293 cells. HEK293 cells were co-transfected with GAL4-LXRα, GAL4-LXRβ or GAL4-GR with UAS-luc reporter plasmid. The $IC_{50}$ of the LXR antagonists (GSK2033, Amgen54, DMHCl) against LXRα or LXRβ was determined using the dual LXR ligand T0901317 co-dosed at the $EC_{80}$ for each receptor (A) 250 nM for GAL4-LXRα and (B) 100 nM for GAL4-LXRβ. (C) GSK2033 did not antagonize the activity of GAL4-GR when activated with 100 nM Dex. Data represent the mean±SD (N=3). $IC_{50}$ values were determined using a sigmoidal curve fit (Prism, GraphPad). RLU=relative luciferase units.

In this experiment, the $IC_{50}$ values to inhibit LXRα were determined to be, 22 nM for GSK2033 and undetermined for Amgen 54 and DMHCl (FIG. 6A). The $IC_{50}$ values to inhibit LXRβ were found to be, 6.44 nM for GSK2033 and 1085 nM and for Amgen 54 (FIG. 6B). DMHCL $IC_{50}$ values could not be accurately determined in this experiment for LXR α and LXRβ. Dex induced GR activity remained unaffected by GSK2033, Amgen 54 and DMHCl (FIG. 6C).

Example 8

Further Studies in Mouse Primary Hepatocytes to Investigate the Gluconeogenic Effects of Dex±LXR Antagonist Treatment (GSK2033 vs. Amgen 54 vs. DMHCl)

To investigate whether antagonism of LXRs by DMHCl and Amgen 54 along with Dex treatment alters GR-mediated gluconeogenic genes, Pepck and G6Pc expression in vitro, a number of gene expression were conducted on mouse primary hepatocytes isolated from LXRα−/− mice.

For the gene expression studies, the isolated hepatocytes were cultured at least 24 hrs prior to treatment with 100 nM Dex±10 μM DMHCL, 100 nM Dex±10 μM Amgen 54 and 100 nM Dex±10 μM GSK2033 overnight, and then harvested to isolate mRNA. Dex-induced Pepck expression was significantly down-regulated by DMHCl (from 15.8 fold to 1.4 fold), Amgen 54 (from 15.8 fold to 8.4 fold) and GSK2033 (from 15.8 fold to 2.7 fold) co-treatment in LXRα−/− primary hepatocytes (FIG. 7A). Furthermore, Dex-mediated G6Pc expression was also dampened by DMHCl (from 10.3 fold to 3.9 fold), Amgen 54 (from 10.3 fold to 6.5 fold) and GSK2033 (from 10.3 fold to 5.3 fold) co-treatment in LXRα−/− primary hepatocytes (FIG. 7B).

Example 9

Treatment with an LXRβ Antagonist in a Mouse Model of Cushing's Disease

Figure 7:
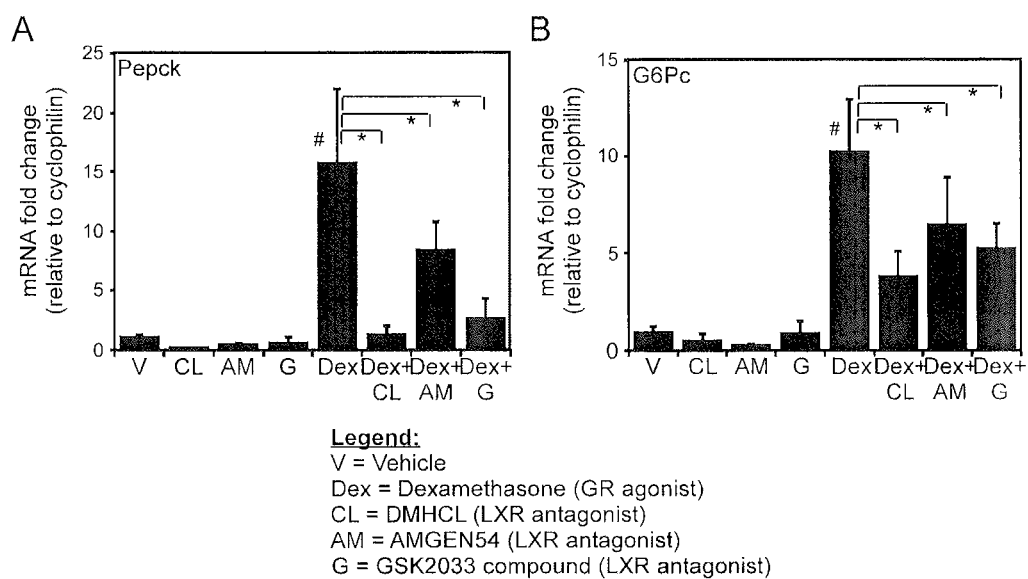
FIG. 7 shows that treatment with GSK2033, Amgen54 or DMHCl results in repression of gluconeogenic gene expression. Expression of (A) Pepck and (B) G6Pc, both gluconeogenic GR target genes, in LXRα–/– mouse primary hepatocytes following 18 hr treatment with Veh, 10 μM GSK2033, 10 μM Amgen54, 10 μM DMHCl and 100 nM Dex alone or in combination. Data is the average±SD of samples derived from three different hepatocyte preparations. #P<0.05 relative to vehicle treatment; *P<0.05 relative to GC treatment alone. One way ANOVA, Student Newman Keuls.
Figure 8:
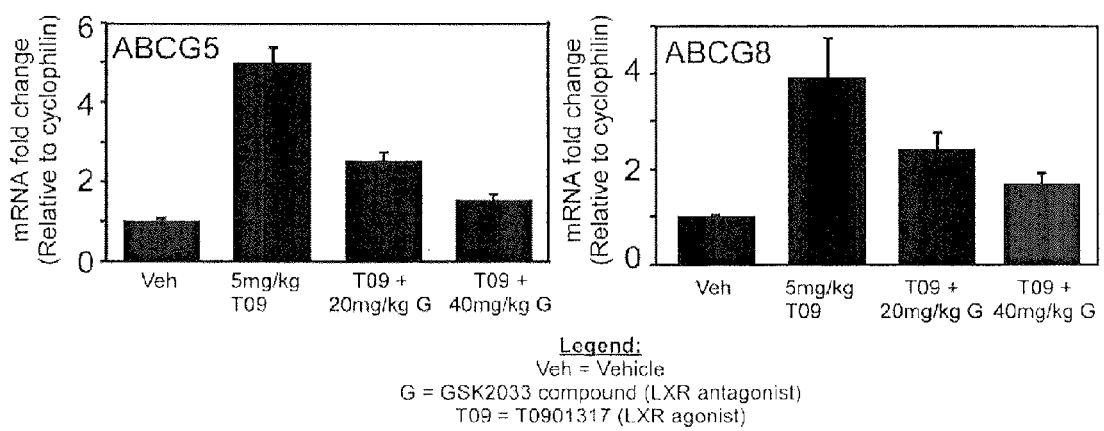
FIG. 8 shows a dose dependent repression of liver LXR target genes, ABCG5 and ABCG8, was observed with T09/GSK2033 co-treatment. LXRα–/– mice were injected i.p. with T09 (5 mg/kg) followed by i.p. injection of 20 or 40 mg/kg GSK2033. Data represents (N=1) mouse per treatment. Data represent Avg±SD of triplicates from QPCR analysis.

As reported in Example 1, the $IC_{50}$ values for GSK2033 in HEK293 cells are 79 nM and 37 nM for LXRα and LXRβ, respectively. When a similar test of GSK2033 inhibitory potency was performed in primary hepatocytes, the $IC_{50}$ values were right-shifted almost 10-fold. These data suggest that GSK2033 is rapidly metabolized in the primary hepatocytes or not efficiently taken up. Given these findings in hepatocytes a pilot study was performed to test the dose of GSK2033 required to inhibit LXR activity in vivo. The LXR ligand T0901317 (T09; 5 mg/kg) was administered by i.p. injection concurrently with vehicle or GSK2033 (20 or 40 mg/kg/day). A dose dependent inhibition of ABCG5 and ABCG8 activation by T09 was observed with co-treatment with GSK2033 indicating in vivo activity of the LXR antagonist (FIG. 7). Since no toxicity was noted at the higher dose of GSK2033 further studies will administer 40 mg/kg GSK2033. CRH-Tg mice (a model for Cushing's disease because these mice exhibit 10-fold higher than normal levels of circulating GCs) are commercially available from Jackson Laboratories (#003210; C57Bl/6 background). The Tg mice are bred in house and C57Bl/6 mice are purchased for the WT controls.

Experiment 1.

In vivo study of vehicle (Veh) or GSK2033 in WT, CRH-Tg mice (dynamic bone labeling and tissue collection): WT and CRH-Tg mice (male, 12 wks old; N=10/group) are treated with vehicle (sesame oil) or GSK2033 (40 mg/kg/day, ip injection) for 28 days. On days 19 and 26, all mice are injected with calcein green (10 mg/kg, s.c. injection), a bone mineralization marker, to determine the rate of bone formation in each group. Mice are sacrificed at lights on by decapitation when endogenous GC levels are at their lowest. At sacrifice, the liver, spleen, adrenal gland, quadriceps, gastrocnemius, and tibialis anterior muscles are weighed and flash frozen in liquid $N_2$ or processed for histology (see below). The following bones are dissected: lumbar vertebrae, femurs, tibias and humeri. Bones are cleaned of soft tissue immediately and stored at −20° C. in saline soaked gauze for phenotype assessment. One femur from each animal is frozen at −80° C. for RNA. Analysis of plasma, liver, muscle and bone are the primary focus of this study but other tissues including white and brown adipose, and heart are kept at −80° C.

Molecular and biochemical assays: Slices of liver are kept for the analysis of tissue triglyceride[27], cholesterol[28] and glycogen levels[29]. Liver RNA is analyzed by QPCR for genes involved in gluconeogenesis and lipogenesis as described previously[27]. Muscle RNA is analyzed for transcript levels of myostatin, MuRF-1 and MAFbx, muscle-specific markers induced by GC treatment (QPCR)[30,31,32,33]. One femur is processed for RNA analysis of osteoprotegerin, RANK-L and osteocalcin.

Histologic analyses: Small pieces of liver are formalin fixed overnight and processed for paraffin embedding for H&E and cryosectioned for oil red O staining. Muscle processed for histology is frozen in liquid $N_2$ cooled isopentane and cryosectioned at 10 μm and stained with laminin (Sigma) to calculate fiber cross-sectional area[30]. The proximal tibia and L3 vertebra are processed for static and dynamic histomorphometry. Briefly, tissues are dehydrated in a graded series of acetone and embedded in Spurr's resin.[34] Histomorphometric analysis is performed using a Leitz Bioquant morphometry system (in Grynpas laboratory). Samples are randomized and blinded prior to analysis.

Static measures of cancellous bone volume and thickness and cellular parameters (osteoclast and osteoblast surface) are performed from undecalcified sections stained with toluidine blue.[35]

Osteoclasts are visualized by Tartrate-Resistant Acid Phosphatase (TRAP) staining of L4 vertebra decalcified with EDTA, embedded in paraffin.[36] Dynamics of bone formation are measured from unstained Spurr's-embedded sections examined in fluorescent light. All histomorphometric data are analyzed and calculated according to the ASBMR nomenclature committee.[37]

Biomarker analyses: Using commercially available colorimetric or RIA kits, plasma is analyzed for glucose (Wako), insulin (Millipore), FFA (Wako), ketone bodies (Ranbut, Randox) cholesterol (Thermo) and triglycerides (Thermo). Plasma lipoproteins are fractionated by FPLC and measured for cholesterol and triglyceride content.[28] Biomarkers of muscle wasting and bone turnover are measured from plasma. Muscle wasting decreases phosphocreatine to creatinine conversion and decreases circulating creatinine. Plasma creatinine will be measured by LC/MS/MS using an established method. Using ELISA, serum levels of bone formation markers (osteocalcin; Immunotopics), and bone resorption markers C-terminal telopeptide (CTX-1; USCN Life Science) and tartrate-resistant acid phosphatase 5b (TRAP-5b, Immunodiagnostics) are measured.[38] Plasma corticosterone (HPA axis) is measured by RIA (MP Biomedical).

Bone phenotype assessment: Dual X-ray absorptiometry (DEXA) scan of the lumbar spine, and femur are performed using a Lunar PIXIMUS.[34] Bone mineral density (BMD) is calculated for vertebrae and femurs. Vertebrae (L5 and L6) are scanned using λCT (Skyscan) to evaluate trabecular bone architecture and volumetric density.[34] Bone strength (resistance to fracture) will be measured on femurs by three point bending.[39, 40] Mineralization will be measured using quantitative back scattered electron imaging.[41,42]

Experiment 2A.

Insulin tolerance test and glucose tolerance test. To assess whether CRH-Tg mice have improved glucose disposal treatment with GSK2033 glucose tolerance and insulin tolerance tests are performed. WT and CRH-Tg mice (male, 12 wks old; N=10/group) are treated with vehicle (sesame oil) or GSK2033 (40 mg/kg/day, ip injection) for 28 days. At day 20, mice are fasted for 4 hr and injected with D-glucose as previously described.[27] A handheld glucometer (Bayer) is used to measure blood glucose at regular intervals. On day 27, the same mice are fasted for 4 hr and injected insulin i.p. for the insulin tolerance test. After a 2 day washout, Expt 2B is performed.

Experiment 2B.

Hepatic insulin signalling in GSK2033-treated mice. Many proteins downstream of insulin signalling are rapidly phosphorylated.[43] To establish whether WT and CRH-Tg mice respond differently to insulin in the presence of GSK2033, WT and CRH-Tg mice are injected i.p. with insulin (1.5 U/kg, 10 min) in mice fasted for 4 hr. Total and phosphorylated levels of IRS-1, IRS-2, Akt, GSK-3β, FOXO1, and FOXO3a are then probed by Western blot.[44, 45, 46]

FULL CITATIONS FOR DOCUMENTS REFERRED TO IN THE APPLICATION

[1] Reid, I. R & Heap, S. W., *Determinants of vertebral mineral density in patients receiving long-term glucocorticoid therapy*. Arch. Intern. Med., 1990. 150: 2545-8.

[2] Arner, P., et al., *Some characteristics of steroid diabetes: A study in renal-transplant recipients receiving high-dose corticosteroid therapy*. Diabetes Care, 1983. 6(1): 23-5.

[3] Puigserver, P., et al., *Insulin-regulated hepatic gluconeogenesis through FOXO1-PGC-1 alpha interaction*. Nature, 2003. 423(6939): p. 550-5.

[4] Cassuto, H., et al., *Glucocorticoids regulate transcription of the gene for phosphoenolpyruvate carboxykinase in the liver via an extended glucocorticoid regulatory unit*. J Biol Chem, 2005. 280(40): p. 33873-84.

[5] Chakravarty, K., et al., *Factors that control the tissue-specific transcription of the gene for phosphoenolpyruvate carboxykinase-C*. Crit. Rev Biochem Mol Biol, 2005. 40(3): p. 129-54.

[6] Commerford, S. R., et al., *Dissection of the Insulin-Sensitizing Effect of Liver X Receptor Ligands*. Mol+ Endocrinol, 2007.

[7] Liu, Y., et al., *Liver X receptor agonist T0901317 inhibition of glucocorticoid receptor expression in hepatocytes may contribute to the amelioration of diabetic syndrome in db/db mice*. Endocrinology, 2006. 147(11): p. 5061-8.

[8] Imai, E., et al., *Glucocorticoid receptor-cAMP response element-binding protein interaction and the response of the phosphoenolpyruvate carboxykinase gene to glucocorticoids*. J Biol Chem, 1993. 268(8): p. 5353-6.

[9] Sugiyama, T., et al., *Structural requirements of the glucocorticoid and retinoic acid response units in the phosphoenolpyruvate carboxykinase gene promoter*. Mol Endocrinol, 1998. 12(10): p. 1487-98.

[10] Scott, D. K., J. A. Mitchell, and D. K. Granner, *The orphan receptor COUP-TF binds to a third glucocorticoid accessory factor element within the phosphoenolpyruvate carboxykinase gene promoter*. J Biol Chem, 1996. 271(50): p. 31909-14.

[11] Scott, D. K., et al., *The repression of hormone-activated PEPCK gene expression by glucose is insulin-independent but requires glucose metabolism*. J Biol Chem, 1998. 273(37): p. 24145-51.

[12] Hall, R. K., F. M. Sladek, and D. K. Granner, *The orphan receptors COUP-TF and HNF-4 serve as accessory factors required for induction of phosphoenolpyruvate carboxykinase gene transcription by glucocorticoids*. Proc Natl Acad Sci USA, 1995. 92(2): p. 412-6.

[13] Wang, J. C., et al., *The molecular physiology of hepatic nuclear factor 3 in the regulation of gluconeogenesis*. J Biol Chem, 2000. 275(19): p. 14717-21.

[14] Miner, J. N. and K. R. Yamamoto, *The basic region of AP-1 specifies glucocorticoid receptor activity at a composite response element*. Genes Dev, 1992. 6(12B): p. 2491-501.

[15] Roesler, W. J., *What is a cAMP response unit?* Mol Cell Endocrinol, 2000. 162(1-2): p. 1-7.

[16] Waltner-Law, M., et al., *Elements of the glucocorticoid and retinoic acid response units are involved in cAMP-mediated expression of the PEPCK gene*. J Biol Chem, 2003. 278(12): p. 10427-35.

[17] Herzog, B., et al., *The Nuclear Receptor Cofactor RIP140 is Required for the Regulation of Hepatic Lipid and Glucose Metabolism by LXR*. Mol Endocrinol, 2007.

[18] Patel, R., et al., *LXRβ is required for glucocorticoid-induced hyperglycemia and hepatosteatosis in mice*. J. Clin. Invest., 2011. 121(1): p. 431-41.

[19] Nieman, L. K. *Diagnostic tests for Cushing's syndrome*. Endocrine Hypertension 970, 112-118 (2002).

[20] Howlett, T. A., Rees, L. H. & Besser, G. M. *Cushing's syndrome*. Clin. Endocrinol. Metab. 14, 911-45 (1985).

[21] Bhansali, A. et al. *Ectopic Cushing's syndrome: experience from a tertiary care centre*. Indian J. Med. Res. 129, 33-41 (2009).

[22] Ohmori, N. et al. *Osteoporosis is more prevalent in adrenal than in pituitary Cushing's syndrome*. Endocr. J. 50, 1-7 (2003).

[23] Mancini, T., Doga, M., Mazziotti, G. & Giustina, A. *Cushing's syndrome and bone*. Pituitary 7, 249-52 (2004).

[24] Kaltsas, G., Manetti, L. & Grossman, A. B. *Osteoporosis in Cushing's syndrome*. Front Horm Res 30, 60-72 (2002).

[25] Zuercher, W. J., et al., *Discovery of tertiary sulfonamides as potent liver X receptor antagonists*. J. Med. Chem., 2010. 53(8): p. 3412-6.

[26] Wagner B. L. et al., *Promoter-specific roles for liver X receptor/corepressor complexes in the regulation of ABCA1 and SREBP1 gene expression*. Mol Cell Biol. 2003 August; 23(16):5780-9.

[27] Patel, R. et al. LXRbeta is required for glucocorticoid-induced hyperglycemia and hepatosteatosis in mice. J Clin Invest 121, 431-41 (2011).

28 Kalaany, N. Y. et al. LXRs regulate the balance between fat storage and oxidation. *Cell Metab* 1, 231-44 (2005).
29 Chan, T. M. & Exton, J. H. A rapid method for the determination of glycogen content and radioactivity in small quantities of tissue or isolated hepatocytes. *Anal Biochem* 71, 96-105 (1976).
30 Watson, M. L. et al. A cell-autonomous role for the glucocorticoid receptor in skeletal muscle atrophy induced by systemic glucocorticoid exposure. *Am J Physiol Endocrinol Metab* 302, E1210-20 (2012).
31 Clarke, B. A. et al. The E3 Ligase MuRF1 degrades myosin heavy chain protein in dexamethasone-treated skeletal muscle. *Cell Metab* 6, 376-85 (2007).
32 Bdolah, Y., Segal, A., Tanksale, P., Karumanchi, S. A. & Lecker, S. H. Atrophy-related ubiquitin ligases atrogin-1 and MuRF-1 are associated with uterine smooth muscle involution in the postpartum period. *Am J Physiol Regul Integr Comp Physiol* 292, R971-6 (2007).
33 Sandri, M. et al. Foxo transcription factors induce the atrophy-related ubiquitin ligase atrogin-1 and cause skeletal muscle atrophy. *Cell* 117, 399-412 (2004).
34 Mousny, M. et al. Fluoride effects on bone formation and mineralization are influenced by genetics. *Bone* 43, 1067-74 (2008).
35 Omelon, S. et al. Control of vertebrate skeletal mineralization by polyphosphates. *PLoS One* 4, e5634 (2009).
36 Kyle, K. A., Willett, T. L., Baggio, L. L., Drucker, D. J. & Grynpas, M. D. Differential effects of PPAR-{gamma} activation versus chemical or genetic reduction of DPP-4 activity on bone quality in mice. *Endocrinology* 152, 457-67 (2011).
37 Dempster, D. W. et al. Standardized nomenclature, symbols, and units for bone histomorphometry: a 2012 update of the report of the ASBMR Histomorphometry Nomenclature Committee. *J Bone Miner Res* 28, 2-17 (2013).
38 Kauh, E. et al. Prednisone affects inflammation, glucose tolerance, and bone turnover within hours of treatment in healthy individuals. *Eur J Endocrinol* 166, 459-67 (2012).
39 Mousny, M. et al. The genetic influence on bone susceptibility to fluoride. *Bone* 39, 1283-9 (2006).
40 Kasra, M., Vanin, C. M., MacLusky, N. J., Casper, R. F. & Grynpas, M.D. Effects of different estrogen and progestin regimens on the mechanical properties of rat femur. *J Orthop Res* 15, 118-23 (1997).
41 Bracci, P. M., Bull, S. B. & Grynpas, M. D. Analysis of compositional bone density data using log ratio transformations. *Biometrics* 54, 337-49 (1998).
42 Chachra, D. et al. The effect of different hormone replacement therapy regimens on the mechanical properties of rat vertebrae. *Calcif Tissue Int* 56, 130-4 (1995).
43 Kim, J. Y. et al. Obesity-associated improvements in metabolic profile through expansion of adipose tissue. *J Clin Invest* 117, 2621-37 (2007).
44 Boissan, M. et al. Overexpression of insulin receptor substrate-2 in human and murine hepatocellular carcinoma. *Am J Pathol* 167, 869-77 (2005).
45 Hall, R. K., Wang, X. L., George, L., Koch, S. R. & Granner, D. K. Insulin represses phosphoenolpyruvate carboxykinase gene transcription by causing the rapid disruption of an active transcription complex: a potential epigenetic effect. *Mol Endocrinol* 21, 550-63 (2007).
46 Sekine, K. et al. Foxo1 links insulin signaling to C/EBPalpha and regulates gluconeogenesis during liver development. *Embo J* 26, 3607-15 (2007).

TABLE 1

Various treatments for GC-induced side effects

| GC-induced side effect | Therapeutic strategy (combined with GC treatment regime) | Weakness in therapeutic approach |
|---|---|---|
| Steroid-induced diabetes | All major classes of oral hypoglycemic agents (OHAs): metformin, sulphonylureas and thiazoledinediones) can be used in steroid-induced diabetes. | Unless the dose of glucocorticoid used is relatively low (for example, 5-10 mg of prednisone), these alone are rarely adequate. |
| | GLP-1: exenatide (Byetta) | Injection, causes nausea, weight loss. |
| | Insulin | Daily injection, monitoring, could cause hypoglycemia, fatty liver disease, etc. |
| | Secretagogues: nateglinide (Starlix) | Wears off overnight. |
| Bone loss | Bisphosphonates: Alendronate and risedronate are the most commonly used. Calcitonin can be considered in patients who cannot tolerate oral or intravenous bisphosphonates. | Brittle bone disease after continued long-term treatment. |
| Myopathy | Discontinuation or reduction of glucocorticoids and aggressive management of medical comorbidities. | Patient may never regain muscle mass. |

The invented claimed is:

1. A method of treating a side effect of elevated glucocorticoid levels comprising administering a therapeutically effective amount of an agent that antagonizes the LXRβ receptor to a subject in need thereof, wherein the agent that antagonizes the LXRβ receptor is GSK2033, or a pharmaceutically acceptable solvates thereof.

2. The method of claim 1, wherein the side effect of elevated glucocorticoid levels is selected from one or more of insulin resistance, hyperglycemia, diabetes, fatty liver, hypertension, bone loss, muscle wasting, muscle weakness, increased appetite, weight gain, deposits of fat in the chest, face, upper back or stomach, water retention or salt retention leading to swelling or edema, high blood pressure, black and blue marks, cataracts, acne, thinning of the skin, stomach ulcers, increased sweating, mood swings, adrenal suppression, adrenal crisis, and psychological problems.

3. The method of claim 2, wherein the side effect of elevated glucocorticoid levels is a gluconeogenic side effect.

4. The method of claim 1, wherein the elevated glucocorticoid levels are the result of elevated endogenous glucocorticoid levels.

5. The method of claim 4, wherein the endogenous glucocorticoid levels are elevated because of the presence of a condition, disease or disorder selected from Cushing's syndrome, type 2 diabetes and chronic stress.

6. The method of claim 1, wherein the elevated glueoeorticoid levels are the results of administration of exogenous glucocorticoid.

7. The method of claim 6, wherein the glucocorticoid is selected from dexamethasone, betamethasone, cortisone, prednisone, prednisolone, methylprednisolone, beclometasone, fludrocortisone, deoxycorticosterone acetate, triamcinolone, and cortisol (hydrocortisone) and pharmaceutically acceptable salts, ester and amide prodrugs and solvates thereof.

8. The method of claim 7, wherein the glucocorticoid is dexamethasone.

9. A method of treating a side effect of elevated glucocorticoid levels comprising administering a therapeutically effective amount of an agent that antagonizes the LXRβ receptor to a subject in need thereof, wherein the agent that antagonizes the LXRβ receptor is Amgen54 or a pharmaceutically acceptable solvate thereof.

10. The method of claim 9, wherein the side effect of elevated glucocorticoid levels is selected from one or more of insulin resistance, hyperglycemia, diabetes, fatty liver, hypertension, bone loss, muscle wasting, muscle weakness, increased appetite, weight gain, deposits of fat in the chest, face, upper back or stomach, water retention or salt retention leading to swelling or edema, high blood pressure, black and blue marks, cataracts, acne, thinning of the skin, stomach ulcers, increased sweating, mood swings, adrenal suppression adrenal crisis, and psychological problems.

11. The method of claim 10, wherein the side effect of elevated glucocorticoid levels is a gluconeogenic side effect.

12. The method of claim 9, wherein the elevated glucocorticoid levels are the result of elevated endogenous glucocorticoid levels.

13. The method of claim 12, wherein the endogenous glucocorticoid levels are elevated because of the presence of a condition, disease or disorder selected from Cushing's syndrome, type 2 diabetes and chronic stress.

14. The method of claim 9, wherein the elevated glucocorticoid levels are the results of administration of exogenous glucocorticoid.

15. The method of claim 14, wherein the glucocorticoid is selected from dexamethasone, betamethasone, cortisone, prednisone, prednisolone, methylprednisolone, beclometasone, fludrocortisone, deoxycorticosterone acetate, triamcinolone, and cortisol (hydrocortisone) and pharmaceutically acceptable salts, ester and amide prodrugs and solvates thereof.

16. The method of claim 15, wherein the glucocorticoid is dexamethasone.

17. A method of treating a side effect of elevated glucocorticoid levels comprising administering a therapeutically effective amount of an agent that antagonizes the LXRβ receptor to a subject in need thereof, wherein the agent that antagonizes the LXRβ receptor is DMHCI OR a pharmaceutically acceptable solvate thereof.

18. The method of claim 17, wherein the side effect of elevated glucocorticoid levels is selected from one or more of insulin resistance, hyperglycemia, diabetes, fatty liver, hypertension, bone loss, muscle wasting, muscle weakness, increased appetite, weight gain, deposits of fat in the chest, face, upper back or stomach, water retention or salt retention leading to swelling or edema, high blood pressure, black and blue marks, cataracts, acne, thinning of the skin, stomach ulcers, increased sweating, mood swings, adrenal suppression, adrenal crisis, and psychological problems.

19. The method of claim 18, wherein the side effect of elevated glucocorticoid levels is a gluconeogenie side effect.

20. The method of claim 17, wherein the elevated glucocorticoid levels are the result of elevated endogenous glucocorticoid levels.

21. The method of claim 20, wherein the endogenous glucocorticoid levels are elevated because of the presence of a condition, disease or disorder selected from Cushing's syndrome, type 2 diabetes and chronic stress.

22. The method of claim 17, wherein the elevated glucocorticoid levels are the results of administration of exogenous glucocorticoid.

23. The method of claim 22, wherein the glucocorticoid is selected from dexamethasone, betamethasone, cortisone, prednisone, prednisolone, methylprednisolone, beclometasone, fludrocortisone, deoxycorticosterone acetate, triamcinolone, and cortisol (hydrocortisone) and pharmaceutically acceptable salts, ester and amide prodrugs and solvates thereof.

24. The method of claim 23, wherein the glucocorticoid is dexamethasone.

* * * * *